(12) United States Patent
Hao et al.

(10) Patent No.: US 9,649,233 B2
(45) Date of Patent: May 16, 2017

(54) ABSORBENT PERSONAL CARE ARTICLES HAVING LONGITUDINALLY ORIENTED LAYERS IN DISCRETE PORTIONS

(75) Inventors: Xueen Hao, Beijing (CN); Lin Miao, Beijing (CN); Chunlei Pu, Beijing (CN)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 14/396,068

(22) PCT Filed: Apr. 25, 2012

(86) PCT No.: PCT/CN2012/074671
§ 371 (c)(1),
(2), (4) Date: Oct. 30, 2014

(87) PCT Pub. No.: WO2013/159295
PCT Pub. Date: Oct. 31, 2013

(65) Prior Publication Data
US 2015/0133884 A1    May 14, 2015

(51) Int. Cl.
*A61F 13/15* (2006.01)
*A61F 13/535* (2006.01)
(Continued)

(52) U.S. Cl.
CPC ...... *A61F 13/535* (2013.01); *A61F 13/47218* (2013.01); *A61F 13/537* (2013.01);
(Continued)

(58) Field of Classification Search
CPC .. A61F 13/47; A61F 13/4702; A61F 13/4704; A61F 13/472; A61F 13/47218;
(Continued)

(56) References Cited

U.S. PATENT DOCUMENTS

| 2,566,451 A | 9/1951 | Julien |
| 2,575,165 A | 11/1951 | Donovan |

(Continued)

FOREIGN PATENT DOCUMENTS

| EP | 0 343 941 B1 | 11/1989 |
| EP | 0 769 284 A1 | 4/1997 |

(Continued)

OTHER PUBLICATIONS

Abstract of Chinese Patent—CN1066776, Dec. 9, 1992, 2 pages.
(Continued)

*Primary Examiner* — Bradley Philips
(74) *Attorney, Agent, or Firm* — Kimberly-Clark Worldwide, Inc.

(57) ABSTRACT

An absorbent article is provided. The article includes at least one additional layer non-integral with the absorbent layer, and positioned upon the absorbent layer. The additional layer includes at least first and second discrete portions positioned along the longitudinal direction. The at least first and second discrete portions are spaced apart from each other along the longitudinal direction. The portions are constructed of the same base sheet material and the first portion at least partially defines an opening therein with an opening inner edge. The second portion is of a shape mated to fit along its periphery edge, at least partially within the opening. The second portion is of a shape complementary with the opening shape. Edges of the first and second portion are complementary, the inner edge of the first portion being complementary with the periphery edge of the second portion.

8 Claims, 13 Drawing Sheets

(51) Int. Cl.
*A61F 13/537* (2006.01)
*A61F 13/84* (2006.01)
*A61F 13/472* (2006.01)
*A61F 13/45* (2006.01)

(52) U.S. Cl.
CPC ........ *A61F 13/53713* (2013.01); *A61F 13/84* (2013.01); *A61F 13/47227* (2013.01); *A61F 2013/15121* (2013.01); *A61F 2013/4581* (2013.01); *A61F 2013/8497* (2013.01)

(58) Field of Classification Search
CPC .............. A61F 13/47227; A61F 13/535; A61F 13/5355; A61F 13/532; A61F 13/53051; A61F 13/530525; A61F 13/530518; A61F 13/530547; A61F 13/530554; A61F 13/530562; A61F 13/495; A61F 13/51186; A61F 13/53765; A61F 13/53769; A61F 13/53773; A61F 13/53778; A61F 13/53445; A61F 13/53454; A61F 13/471; A61F 13/47209; A61F 13/47272; A61F 13/47236; A61F 13/491; A61F 13/4915; A61F 13/4953; A61F 13/4958; A61F 13/537; A61F 13/53713; A61F 13/4581; A61F 13/4568
See application file for complete search history.

(56) References Cited

U.S. PATENT DOCUMENTS

| | | |
|---|---|---|
| 3,073,309 A | 1/1963 | Mosier |
| 3,343,543 A | 9/1967 | Glassman |
| 3,441,023 A | 4/1969 | Rijssenbeek |
| 3,545,441 A | 12/1970 | Gravdahl |
| 3,828,786 A | 8/1974 | Cervantes |
| 3,881,490 A | 5/1975 | Whitehead et al. |
| 3,889,679 A | 6/1975 | Taylor |
| 3,913,580 A | 10/1975 | Ginocchio |
| 4,184,498 A | 1/1980 | Franco |
| 4,285,342 A | 8/1981 | Mesek |
| 4,337,772 A | 7/1982 | Roeder |
| 4,375,448 A | 3/1983 | Appel et al. |
| 4,376,799 A | 3/1983 | Tusim |
| 4,397,644 A | 8/1983 | Matthews et al. |
| 4,494,278 A | 1/1985 | Kroyer et al. |
| 4,501,586 A | 2/1985 | Holtman |
| 4,531,945 A | 7/1985 | Allison |
| 4,556,146 A | 12/1985 | Swanson et al. |
| 4,578,069 A | 3/1986 | Whitehead et al. |
| 4,610,678 A | 9/1986 | Weisman et al. |
| 4,624,666 A | 11/1986 | DeRossett et al. |
| 4,629,643 A | 12/1986 | Curro et al. |
| 4,631,062 A | 12/1986 | Lassen et al. |
| 4,640,810 A | 2/1987 | Laursen et al. |
| 4,673,403 A | 6/1987 | Lassen et al. |
| 4,731,065 A | 3/1988 | Yamada |
| 4,781,710 A | 11/1988 | Megison et al. |
| 4,795,455 A | 1/1989 | Luceri et al. |
| 4,988,344 A | 1/1991 | Reising et al. |
| 4,988,345 A | 1/1991 | Reising |
| 5,171,302 A | 12/1992 | Buell |
| 5,176,672 A | 1/1993 | Bruemmer et al. |
| 5,188,625 A | 2/1993 | Van Iten et al. |
| 5,252,619 A | 10/1993 | Brownscombe et al. |
| 5,300,055 A | 4/1994 | Buell |
| 5,304,161 A | 4/1994 | Noel et al. |
| 5,348,547 A | 9/1994 | Payne et al. |
| 5,364,382 A | 11/1994 | Latimer et al. |
| 5,366,451 A | 11/1994 | Levesque |
| 5,382,400 A | 1/1995 | Pike et al. |
| 5,397,316 A | 3/1995 | LaVon et al. |
| 5,415,640 A | 5/1995 | Kirby et al. |
| 5,462,537 A | 10/1995 | Carr et al. |
| 5,527,171 A | 6/1996 | Soerensen |
| 5,533,991 A | 7/1996 | Kirby et al. |
| 5,591,153 A * | 1/1997 | Mattingly, III ... A61F 13/15747 604/385.05 |
| 5,662,633 A | 9/1997 | Doak et al. |
| 5,692,939 A | 12/1997 | DesMarais |
| 5,695,849 A | 12/1997 | Shawver et al. |
| 5,743,896 A | 4/1998 | Parker |
| 5,755,710 A | 5/1998 | Menard |
| 5,762,641 A | 6/1998 | Bewick-Sonntag et al. |
| 5,795,344 A | 8/1998 | Chappell |
| 5,810,798 A | 9/1998 | Finch et al. |
| 5,820,619 A | 10/1998 | Chen |
| 5,830,203 A | 11/1998 | Suzuki et al. |
| 5,836,929 A | 11/1998 | Bewick-Sonntag et al. |
| 5,843,063 A | 12/1998 | Anderson et al. |
| 5,855,719 A | 1/1999 | Menard |
| 5,899,893 A | 5/1999 | Dyer et al. |
| 5,961,505 A | 10/1999 | Coe et al. |
| 6,011,195 A | 1/2000 | Muhs et al. |
| 6,059,710 A | 5/2000 | Rajala et al. |
| 6,060,636 A | 5/2000 | Yahiaoui et al. |
| 6,074,333 A | 6/2000 | Rajala et al. |
| 6,075,179 A | 6/2000 | McCormack et al. |
| 6,077,254 A | 6/2000 | Silwanowicz et al. |
| 6,117,523 A | 9/2000 | Sugahara |
| 6,165,306 A | 12/2000 | Rajala |
| 6,171,432 B1 | 1/2001 | Brisebois et al. |
| 6,241,714 B1 | 6/2001 | Raidel et al. |
| D448,481 S | 9/2001 | Mok |
| 6,284,942 B1 | 9/2001 | Rabin |
| 6,312,416 B1 * | 11/2001 | Brisebois ............ A61F 13/4704 604/358 |
| 6,376,095 B1 | 4/2002 | Cheung et al. |
| 6,395,792 B1 | 5/2002 | Nagasuna et al. |
| 6,410,823 B1 | 6/2002 | Daley et al. |
| 6,548,732 B2 | 4/2003 | Erdman et al. |
| 6,610,903 B1 | 8/2003 | Latimer et al. |
| D483,485 S | 12/2003 | Phillips-Nicholas |
| 6,673,418 B1 | 1/2004 | DeOlivera et al. |
| 6,759,567 B2 | 7/2004 | Colman et al. |
| 6,786,893 B2 | 9/2004 | Strand |
| 6,811,239 B1 | 11/2004 | Salacz |
| 6,911,574 B1 | 6/2005 | Mizutani |
| 6,913,599 B2 | 7/2005 | Mishima et al. |
| 6,984,225 B2 | 1/2006 | Raidel et al. |
| 7,037,298 B2 | 5/2006 | Ohshima et al. |
| 7,067,711 B2 | 6/2006 | Kuroda et al. |
| 7,145,054 B2 | 12/2006 | Zander et al. |
| 7,156,832 B2 | 1/2007 | Drevik et al. |
| 7,358,282 B2 | 4/2008 | Krueger et al. |
| 7,387,620 B2 | 6/2008 | Watanabe et al. |
| 7,402,157 B2 | 7/2008 | Christon et al. |
| D600,798 S | 9/2009 | Hood et al. |
| D600,799 S | 9/2009 | Hood et al. |
| D600,800 S | 9/2009 | Hood et al. |
| D600,802 S | 9/2009 | Hood et al. |
| D600,804 S | 9/2009 | Hood et al. |
| 7,594,905 B2 | 9/2009 | Tanio et al. |
| 7,597,690 B2 | 10/2009 | Tanio et al. |
| D612,491 S | 3/2010 | Sullivan Conrad et al. |
| 7,686,790 B2 | 3/2010 | Rasmussen et al. |
| D630,316 S | 1/2011 | Hood et al. |
| 7,976,525 B2 | 7/2011 | McDaniel |
| 7,982,091 B2 | 7/2011 | Konawa |
| 8,016,803 B2 | 9/2011 | Mueller et al. |
| 8,039,685 B2 | 10/2011 | Mason, Jr. et al. |
| 8,142,876 B2 | 3/2012 | Ueminami et al. |
| 8,211,078 B2 | 7/2012 | Noel |
| 8,293,966 B2 | 10/2012 | Obele |
| 8,317,768 B2 | 11/2012 | Larsson |
| 8,536,401 B2 | 9/2013 | Ecker et al. |
| 8,541,644 B2 | 9/2013 | Raidel et al. |
| 8,754,286 B2 | 6/2014 | Bergström et al. |
| 2003/0078553 A1 | 4/2003 | Wada et al. |
| 2003/0125701 A1 | 7/2003 | Widlund |
| 2003/0130643 A1 * | 7/2003 | Drevik ................ A61F 13/4702 604/385.31 |
| 2003/0153232 A1 | 8/2003 | Raidel et al. |

(56) References Cited

U.S. PATENT DOCUMENTS

| | | | |
|---|---|---|---|
| 2004/0111074 A1* | 6/2004 | Eliasson | A61F 13/535 604/367 |
| 2004/0133179 A1 | 7/2004 | Steger et al. | |
| 2004/0170813 A1 | 9/2004 | Digiacomantonio et al. | |
| 2005/0131369 A1* | 6/2005 | Benson | A61F 13/20 604/385.01 |
| 2006/0287635 A1 | 12/2006 | Angel, Jr. | |
| 2007/0055210 A1 | 3/2007 | Kao | |
| 2007/0073255 A1 | 3/2007 | Thomas et al. | |
| 2007/0087169 A1 | 4/2007 | McFall | |
| 2007/0135787 A1 | 6/2007 | Raidel et al. | |
| 2008/0071237 A1 | 3/2008 | Chen et al. | |
| 2008/0208154 A1* | 8/2008 | Oetjen | D04H 3/00 604/367 |
| 2008/0243100 A1 | 10/2008 | Wu et al. | |
| 2010/0174260 A1 | 7/2010 | Di Luccio et al. | |
| 2010/0256586 A1 | 10/2010 | Bergstrom et al. | |
| 2011/0060303 A1 | 3/2011 | Bissah et al. | |
| 2012/0010584 A1* | 1/2012 | Schmidt | A61F 13/0226 604/372 |
| 2012/0157952 A1 | 6/2012 | Poruthoor et al. | |
| 2012/0220972 A1 | 8/2012 | Kawamura et al. | |
| 2012/0277711 A1 | 11/2012 | Kim et al. | |
| 2013/0231628 A1 | 9/2013 | Dieringer et al. | |
| 2013/0245589 A1 | 9/2013 | Toda et al. | |
| 2013/0338621 A1 | 12/2013 | Ecker et al. | |
| 2014/0128828 A1 | 5/2014 | Andersson et al. | |

FOREIGN PATENT DOCUMENTS

| | | |
|---|---|---|
| EP | 0 934 737 A1 | 8/1999 |
| GB | 1 349 962 | 4/1974 |
| GB | 1595393 A | 8/1981 |
| GB | 2284767 A | 6/1995 |
| GB | 2283428 A | 10/1995 |
| GB | 2 370 780 A | 7/2002 |
| JP | 59-85661 | 5/1984 |
| JP | 1-122727 | 8/1989 |
| JP | 06-031722 | 4/1994 |
| JP | 07-012119 | 2/1995 |
| RU | 2362527 | 7/2009 |
| WO | WO 9109582 A1 | 7/1991 |
| WO | WO 9211830 A2 | 7/1992 |
| WO | WO 9701998 A1 | 1/1997 |
| WO | WO 0037002 A1 | 6/2000 |
| WO | WO 0069481 A1 | 11/2000 |
| WO | WO 0069482 A1 | 11/2000 |
| WO | WO 0069483 A1 | 11/2000 |
| WO | WO 0069484 A1 | 11/2000 |
| WO | WO 0069485 A1 | 11/2000 |
| WO | WO 03/015682 A1 | 2/2003 |
| WO | WO 03/015684 A1 | 2/2003 |
| WO | WO 2006/105305 A1 | 10/2006 |
| WO | WO 2008146222 A1 | 12/2008 |
| WO | WO 2009067059 A1 | 5/2009 |
| WO | WO 2013002686 A1 | 1/2013 |
| WO | WO 2013185800 A1 | 12/2013 |

OTHER PUBLICATIONS

Abstract of Chinese Patent—CN201143260, Nov. 5, 2008, 1 page.
Abstract of Chinese Patent—CN202078469, Dec. 21, 2011, 1 page.
Abstract of Chinese Patent—CN102614049. Aug. 1, 2012, 1 page.
Abstract of European Patent—EP0119919, Sep. 26, 1984, 1 page.
Abstract of Japanese Patent—JP11042250, Feb. 16, 1999, 1 page.
Abstract of Japanese Patent—JP2004033325, Feb. 5 2004, 2 pages.
Abstract of Japanese Patent—JP2006239162, Sep. 14, 2006, 2 pages.
Abstract of Japanese Patent—JP2007050145, Mar. 1, 2007, 1 page.
Abstract of Japanese Patent—JP2009112864, May 28, 2009, 1 page.
Machine Translation of European Patent—EP0164595, Dec. 18, 1985, 6 pages.
Machine Translation of French Patent—FR2420339, Oct. 19, 1979, 5 pages.
Machine Translation of Japanese Patent—621624, Jun. 3, 1994, 6 pages.
Translation of Japanese Patent—JPH11076304 A2, Mar. 23, 1999, 8 pages.
Translation of Japanese Patent—JP59190229, 5 pages.
Abstract of Japanese Patent—JP2006051211, Feb. 23, 2006, 2 pages.
International Search Report for PCT/CN2012/074671 dated Nov. 9, 2012, 2 pages.

* cited by examiner

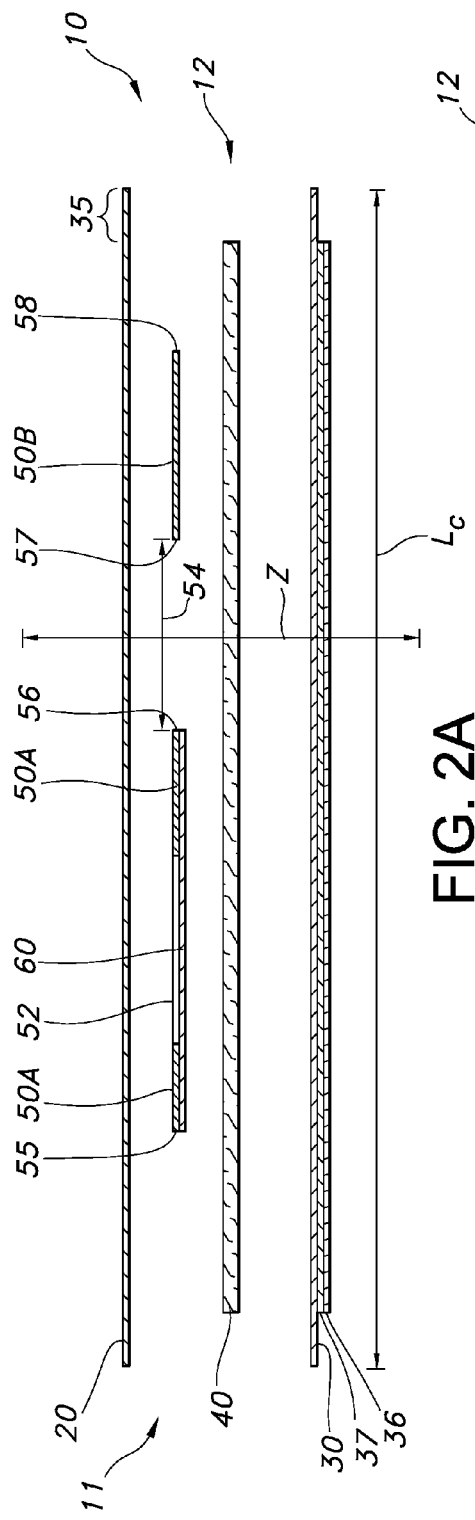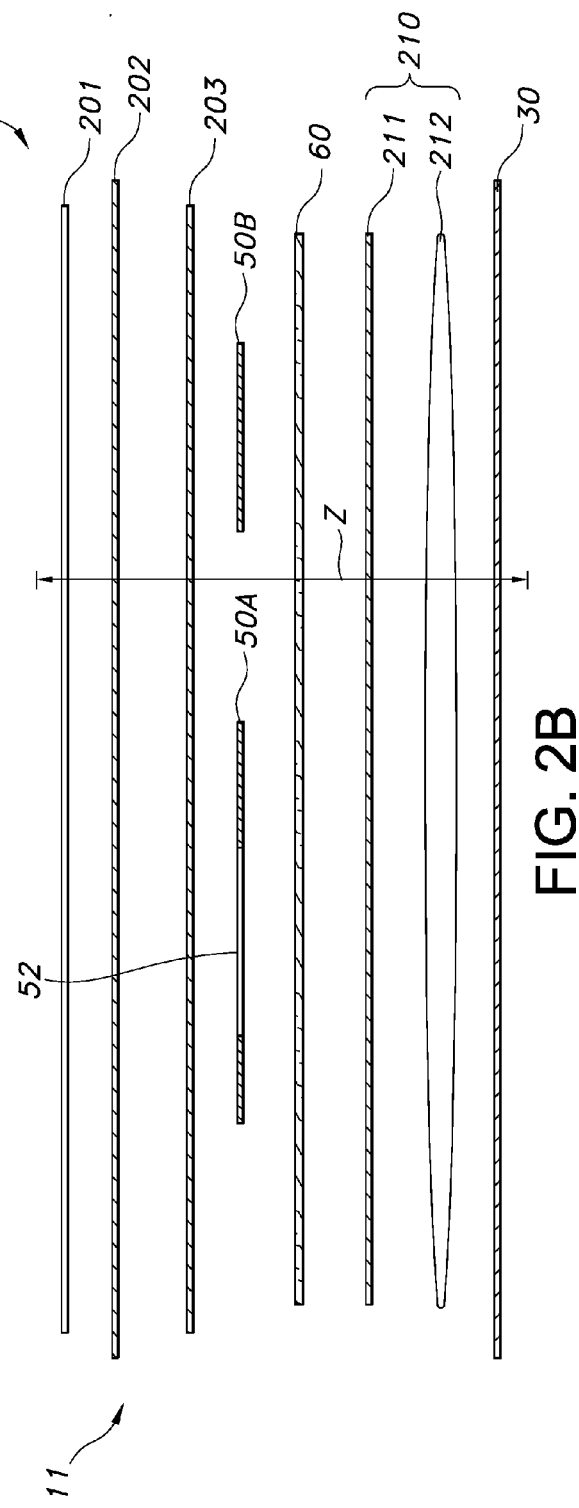

ABSORBENT PERSONAL CARE ARTICLES HAVING LONGITUDINALLY ORIENTED LAYERS IN DISCRETE PORTIONS

CROSS REFERENCE TO RELATED APPLICATION

This application is the national stage entry of International Patent Application No. PCT/CN2012/074671 having a filing date of Apr. 25, 2012, the entire contents of which is incorporated herein by reference.

FIELD OF THE INVENTION

The present invention relates to absorbent personal care articles. More particularly, it relates to absorbent personal care articles having layers oriented along the article longitudinal direction, the absorbent personal care articles designed for placement in undergarments and articles of clothing.

BACKGROUND

Absorbent personal care articles such as sanitary napkins and pads, panty liners, adult incontinence garments and pads, baby and child care diapers and pants, commonly utilize a layered structure construction to direct and collect body exudates, as well as to configure the article for a comfortable fit adjacent a user's body.

The manufacturers of these articles have developed numerous structural features to address problems of leakage. Such structures may define openings in upper layers to allow body exudates to pass directly to lower absorbent core layers after initial fluid deposition, such as from a user's genital or anal regions. Such openings, apertures or recesses in absorbent articles are described for example, in U.S. Pat. No. 4,988,345 to Reising and U.S. Pat. No. 5,810,798 to Finch et al.; U.S. Pat. Nos. 6,241,714 and 6,984,225 to Aschenbrenner, and JP2006-51211. While such openings have proven somewhat effective for collecting fluid in a well-like structure, and for directing exudates to deeper article locations, leakage continues to be a problem with these articles. Further, manufacturing constraints and material costs have often prevented usage of these features with other desirable absorbent article topographical structures. Additionally, use of layers with openings has led to manufacturing material waste, as such layers by necessity, have unused center portions. There is a need for articles with such features, with improved leakage protection, that reduce manufacturing-material waste, and that also allow for the introduction of other article topographical structures.

Such desirable topographical features include raised components or hump-like elements, to enhance an article's close-to-body fit, such as for example, those humps described in JP2006-239162, and GB 2370780 to Aschenbrenner. Such hump-like features have been described in multiple shapes, depending on article configuration. It has been found that such hump features 1) elevate portions of an absorbent article to a position closer to a fluid deposition region, 2) provide controls on how the article might bend or turn when in use (as an article shaping layer/element), and also 3) provide a stabilizing or rigidifying element, such as a slide-prevention element for certain articles when the hump is positioned under certain regions of a user's body. Such element could help retain for example, an absorbent article positioned between the buttocks of a user during sleep. These layered structures are often produced inefficiently from different types of materials than the rest of the article layers, adding to overall article costs. There is therefore a continued need for absorbent articles with efficiently constructed topographical features, such as humps.

Further, while different layer structures have been developed by manufacturers to facilitate rapid absorbency, or improved fit, such as shaping layers, these structures often result in material waste during the manufacturing process, as excess material is often unable to be used after the structure is cut from a material base sheet, and such excess material is subsequently discarded. While numerous techniques have been developed for conserving manufacturing base sheet material during an article's manufacture, such as those described in U.S. Pat. No. 6,171,432 to Brisebois et al., such techniques and methods have focused on use of continuous, side-by-side strips of material for placement in absorbent articles. Thus, there exists a need for an absorbent personal care article having a layered structure with multiple topographical features, and which is manufactured with reduced material waste.

Absorbent articles, such as sanitary napkins have been previously described to include both a hump and groove structure. Such combination of features is described in U.S. Pat. No. 5,820,619 to Chen, which details the hump, as a projecting and relatively narrow "stop element", for the purposes of holding a feminine care product in the coccyx area of a user in order to absorb menstrual discharge. The paired, relatively narrow groove element described in the Chen reference, is included for the sole purpose of holding the hump, when the article is stored in a folded configuration, such that the article is retained in a flat, folded orientation, while not in use. The stop element is described as being formed integrally from the absorbent body structure, such that its construction and material properties are limited by the material of the absorbent body structure. Therefore, a continued need exists for an absorbent article which offers multiple topographical features, and which is not limited by the material properties of other absorbent layer structures.

SUMMARY OF THE INVENTION

The present invention addresses problems experienced with absorbent articles related to leakage and manufacturing material waste, by providing articles having a layer separated into at least two discrete portions along the article longitudinal direction, with the two portions of the layer made from the same material. As a result of portion shape differences and different portion location placement, such portions provide different functionality to the absorbent article. In a first embodiment, an absorbent article having a longitudinal, transverse and depth direction includes a backsheet layer and at least one absorbent core layer positioned upon the backsheet layer in the depth direction. The article further includes at least one additional layer non-integral with the absorbent layer of the absorbent article, and positioned upon the absorbent layer, wherein the additional layer includes at least first and second discrete portions positioned along the longitudinal direction. The at least first and second discrete portions are spaced apart from each other along the longitudinal direction. The portions are constructed of the same base sheet material, wherein the first portion at least partially defines an opening therein with an opening edge, and further wherein the second portion is of a shape mated to fit at least partially within the opening.

In an alternative of the absorbent article, the shape of the at least partial opening of the first portion is complementary to the shape of the second portion. In yet another alternative of the absorbent article, the shape of the complete opening of the first portion is complementary to the shape of the second portion. In still a further alternative of the absorbent article, the shape of the at least partial opening of the first portion is complementary to the shape of a section of the second portion. In still a further alternative embodiment of the absorbent article, the shape of the first portion is complementary to the shape of the second portion.

In a further alternative embodiment of the absorbent article, the shapes of first and second portions are each complementary with the shape of a third portion, and the shape of the third portion is complementary with both the shapes of the first and second portions.

In still a further alternative of the absorbent article, the article further includes a topsheet layer and the absorbent layer is sandwiched between the topsheet layer and the backsheet layer. In such alternative, the additional layer is selected from a shaping layer, an absorbent layer, and a fluid guide layer.

In still a further alternative, the absorbent article includes a front end and a rear end, and the first portion is located towards the front end of the article and the second portion is located towards the rear end of the article. In such an alternative, the first portion directs body exudates to the absorbent core layer and the second portion provides close-to-body fit for the absorbent article. The close to body fit is achieved by a hump-like or raised structure, constructed of the second portion.

In yet a further alternative, the first portion defines a complete opening, as opposed to a partial opening. In yet a further alternative, the first portion defines an oval opening. In still a further alternative, the additional layer is formed from an airlaid base sheet material. In yet another alternative, a printed layer is positioned between the absorbent core layer and the additional layer. In still another alternative, the additional layer is of a color that is visible through the topsheet layer. In still another alternative embodiment, the article is selected from a feminine hygiene article such as an overnight pad, an adult incontinence article, a baby care article and a child care article.

In still a further alternative embodiment, the at least first and second discrete portions of the additional layer are located within the same horizontal plane along the longitudinal direction of the article. In yet a further alternative embodiment, the at least first and second discrete portions of the additional layer are located in different horizontal planes along the longitudinal direction of the article. In still a further alternative, the additional layer includes at least three discrete portions located along the longitudinal direction of the article.

In still a further alternative, the first portion of an additional layer having three portions, defines a partial opening therein, the third portion defines a partial opening therein, and the second portion, positioned between the first and third portions along the longitudinal direction of the article, is of a shape mated to fit within the partial openings of both the first and third portions. In an alternative, the second portion of three is of an oval shape.

In yet another alternative embodiment of the invention, an absorbent article has a longitudinal and transverse direction, and includes a topsheet layer, a backsheet layer and at least one absorbent layer sandwiched between the topsheet layer and the backsheet layer. The absorbent layer includes at least first and second portions positioned along the longitudinal direction, and the at least first and second portions are non-integral with any other layer and spaced apart from one another along the longitudinal direction of the article. The portions are made from the same base sheet material. The first portion defines at least a partial opening therein, and the second portion is of a shape mated to fit at least partially within the partial opening.

In still another alternative embodiment of the invention, an absorbent article has a longitudinal and transverse direction, and includes a topsheet layer, a backsheet layer and at least one absorbent layer sandwiched between the topsheet layer and the backsheet layer. The absorbent layer includes at least first and second portions positioned along the longitudinal direction, and the at least first and second portions are non-integral with any other layer within the article and spaced apart from one another along the longitudinal direction. In such an embodiment the portions are made from the same base sheet material. The first portion defines a complete opening therein, and the second portion is of a shape mated to fit entirely within the opening. The complete opening shape and the second portion shape are complementary.

In yet another embodiment of the invention the first portion is located towards the front end of the article, and the second portion is located towards the rear end of the article, the first portion is shaped and located to fit about a user's vaginal opening and the second portion is shaped and located to fit between a user's buttocks region.

In still another embodiment of the invention, an absorbent article having a longitudinal and transverse direction includes a topsheet layer, a backsheet layer and at least one absorbent layer sandwiched between said topsheet layer and said backsheet layer. The absorbent layer includes at least first, second and third portions positioned along the longitudinal direction, with the at least first, second and third portions being non-integral with any other layer within the article. The portions are spaced apart from one another along the longitudinal direction, with the second portion situated between the first and third portions along the longitudinal direction. The portions are made from the same base sheet material. Additionally, the first and third portions each define a partial opening therein, and the second portion is of a shape mated to fit entirely within the partial openings of the first and third portions.

In still yet another embodiment of the invention, an absorbent article includes a topsheet layer, a backsheet layer, and an absorbent layer positioned between the topsheet layer and the backsheet layer. The absorbent article includes a longitudinal direction, a transverse direction and a depth direction. An additional layer including two or more discrete portions oriented along the longitudinal direction, is positioned between the topsheet layer and the absorbent layer. The two or more portions are non-integral with any layer within the article, are of the same base sheet material, and include complementary edges. In a further alternative embodiment, the complementary edges of the two or more portions include an inner edge of a first portion and a periphery edge of a second portion. In a further alternative embodiment, the complementary edges of the two or more portions include a periphery edge of a first portion and a periphery edge of a second portion. In a further alternative embodiment, the portions number three, and the complementary edges of each of the portions are periphery edges.

BRIEF DESCRIPTION OF THE DRAWINGS

FIG. 2A is a cross-sectional, exploded view of the feminine hygiene overnight pad of FIG. 1 taken along lines 2A-2A (along the longitudinal central axis).

FIG. 2B is a cross-sectional, exploded view of an alternative embodiment of the feminine hygiene overnight pad of FIG. 1 taken along lines 2B-2B, approximately at the longitudinal central axis.

DESCRIPTION OF THE INVENTION

Figure 1:
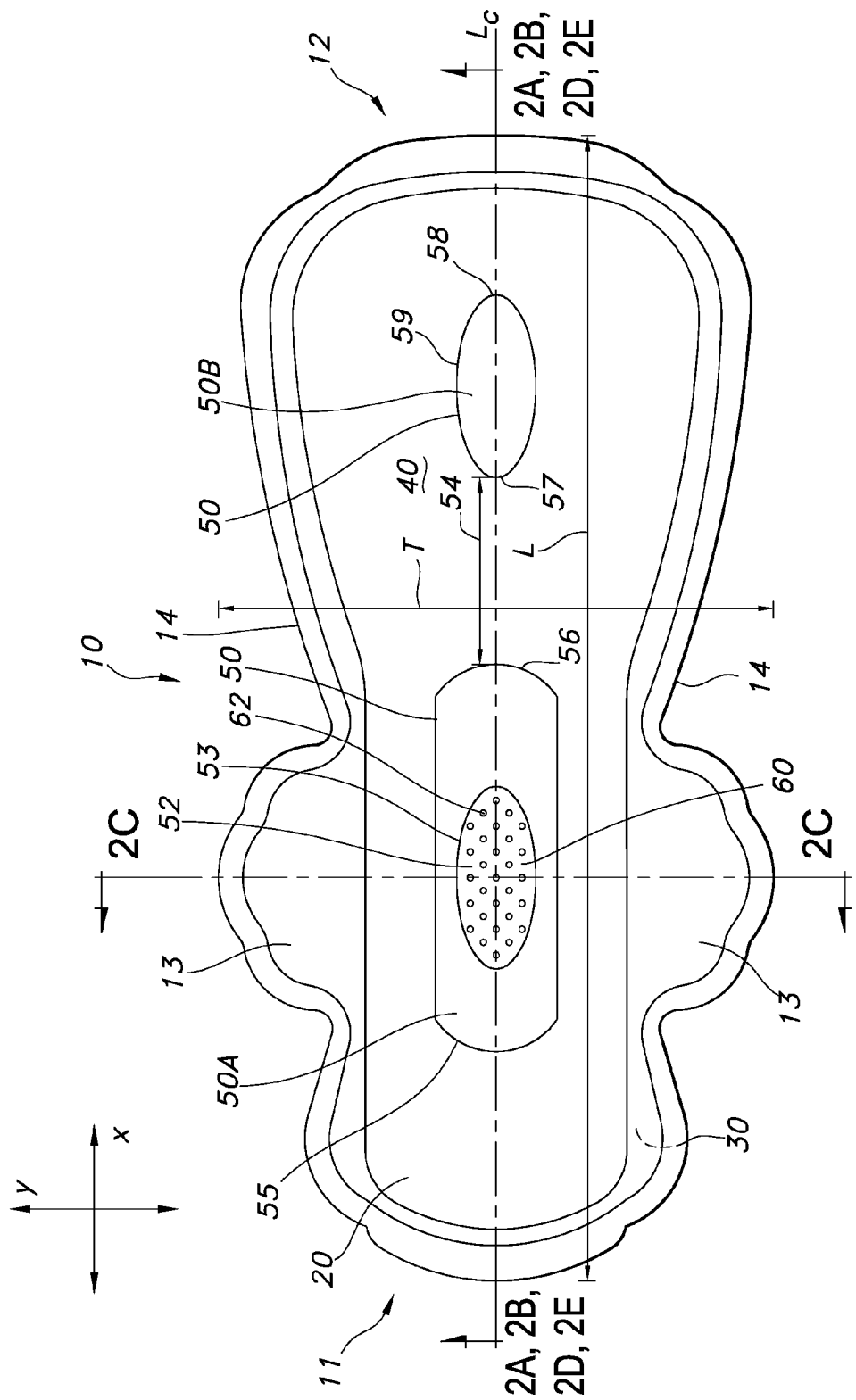
FIG. 1 is a top plan view of one embodiment of an absorbent article of the present invention, in the form of a feminine hygiene overnight pad, in a flat and unfolded state.

It should be understood that the described invention may be applied to a wide variety of disposable personal care, absorbent articles, such as for example, feminine hygiene absorbent articles, adult care absorbent articles, and baby or child-care related absorbent articles. For example, such feminine hygiene absorbent articles include sanitary napkins, pads and liners, such adult care absorbent articles include incontinence garments, pads and inserts, and baby or child-care related absorbent articles include diapers, pants, inserts and bed coverings. In the case of personal care absorbent articles for the collection of body exudates, such articles are typically worn under a user's clothing so as to avoid the fouling of a user's garments by such exudates. While not being limited by one structure, such absorbent articles often include at least two layers in their structure, and more often three or more layers. For example, such articles may include an optional user facing topsheet layer, a liquid impervious, garment-facing or bedding-facing backsheet layer, and at least one absorbent layer sandwiched between the topsheet layer (if present) and the backsheet layer, with the absorbent layer placed upon the backsheet layer in the article depth direction. Often other layers, such as multiple absorbent layers, fluid transfer or fluid delay layers, fluid surge layers, fluid guide layers, article shaping layers or a combination thereof, are present in such articles to provide the absorbent articles with additional functionality.

For the purposes of this application, the terms "upon" or "placed upon" shall be synonymous, and shall encompass not only the situation where one layer is placed immediately or directly upon the surface of another layer, in that one layer surface is placed immediately on, or bonded directly to the surface of another layer in an article depth direction, via conventional bonding of the layers together at their interface (two layers being directly bonded via thermal, adhesive, needle punched, or ultrasonic bonding), but also the situation in which a first layer is placed indirectly on a second layer in the article depth direction. In such a situation, the first and second layers may be separated not only by an adhesive layer, but also by additional layers that are sandwiched between the first and second layers.

For purposes of this application, the phrases "at least partial" or "at least partially" shall be synonymous in their meaning, as to an "opening", and with the word "opening", shall mean a hole, cutout, notch or aperture, through opposite surfaces of a relatively planar base sheet material, which is either completely bounded by a defining, inner edge (such that the cut-out is surrounded by 360° of base sheet material along the X-Y plane) thereby forming a complete opening, or alternatively, an opening through opposite surfaces of a base sheet material, which opening is only partially surrounded by a defining edge, such that the opening is not completely bounded by a base sheet material edge (thereby forming a partial opening). For example, in such a partial opening, the base sheet material of an additional layer portion would surround the opening at some value less than 360°, such as greater than 180°, but less than 360°. The degrees of which the base sheet material surrounds the opening or partial opening would be based on the X-Y plane. Such opening may be created, for example by cutting or punching out regions of the base sheet material. For the purposes of this application, an "opening" does not encompass the interstitial spaces or voids formed during the initial manufacture of base sheet materials, such as the cells formed in foam sheet materials, the spaces between fibers of a nonwoven sheet, or the pockets formed in filled-film sheets. The term "opening" specifically refers to a hole, cutout, notch or aperture. Such hole, cutout, notch or aperture is a spatial feature created in a base sheet material after the initial sheet formation process, such opening formed as by cutting, punching, removal of material from, or other act of physical separation (the post-formation, removal of material from the base sheet). Desirably, in one embodiment for such post-formation hole creation, the shape of a first portion is identified and/or created on a base sheet, and at some stage, a second portion is removed from within the confines of the first portion (for a complete opening formation), or alternatively, from a portion of the confines of the first portion (for a partial opening formation).

Examples of such "at least partial" opening shapes (or partial openings) include, but are not limited to, a material base sheet with an opening having a configuration in the shape of a "C" or "U" in which a void space is generally surrounded by material, but not 360° of material in the X-Y plane, as would be present in a completely bounded opening, shaped like an oval or circular "0", a square, rectangle, triangle or other closed geometric shape. It should also be understood, that the edges defining such opening or at least partial opening, need not be curvilinear, as in a circle, oval or elliptical shape, but may also be symmetrical, but angular, such in a square or rectangle shape. Such partial or complete opening may be asymmetrical as well. Additional opening shapes include for example, toy shapes, animal shapes and other shapes from nature, such as a crescent moon, star, sun, tear drop or leaves.

For purposes of this application, the term "discrete" shall mean a separate, unconnected piece of base sheet material, when placed within the absorbent article. Multiple discrete portions will desirably in one embodiment, have a gap or space separating them along the article longitudinal direction, such gap or space being a feature in which the base sheet material is completely absent. In one embodiment, such base sheet material is desirably absent completely across the article transverse axis, specifically at that gap location.

For the purposes of this application, the term "integral" shall mean a unitary structure, or part of a layer, such as an extension or protuberance, that is of the same material as the remainder of the layer, and extends from the remainder of the layer, not having been attached to the remainder of the layer by any adhesive, thermal, ultrasonic, needle punch or other conventional bonding technique. The term "non-integral" shall mean a non-unitary structure or first layer that is either not attached or otherwise bonded to a second layer, or alternatively, is bonded via adhesive, thermal, ultrasonic, needle punch or other conventional bonding technique to a second layer. In one embodiment, a non-integral first layer is merely positioned upon a second layer.

For the purposes of this application, the term "base sheet" shall mean a generally planar sheet of a fabric, foam, or textile material, or a combination thereof. In one embodiment, such base sheet is in the form of a strip or ribbon of material. In another embodiment, such base sheet is desirably flat or relatively flat, with no elevated surface topography beyond the sheet—formation surface texture of the fabric, foam or textile. In a further embodiment, such base sheet is relatively flat, not having extensions, protrusions or protuberances in the Z direction of the sheet which extend higher than 100% of the thickness of the sheet material in the Z direction. Such protuberances are not meant to encompass conventional surface elevations created by embossing of the fabric, foam or textile.

For the purposes of this application, the term "complementary shape" shall mean a shape that fits together with precision with another shape, like a hand in a glove, or a key into a lock. As a further example, the mated shapes and edges of the pieces of a jigsaw puzzle are also considered complementary shapes and complementary edges for the purposes of this application. A "complementary edge" shall mean an edge that fits together with precision with another edge.

In reference to FIGS. 1 and 2A, the drawings show one embodiment of the absorbent personal care articles of the present invention, in the form of a feminine hygiene overnight pad 10 in a flat and unfolded state. While feminine hygiene articles are illustrated in the figures, the invention may also be applied to any of the previously described absorbent article product types. Except as otherwise noted, discussion of dimensions of the article and/or the positions of individual components thereof are in reference to the article being in a flat and unfolded state. Further, as used herein, the terms "comprising" or "including" are inclusive or open-ended and do not exclude additional unrecited elements, compositional components, or method steps. Accordingly, the terms "comprising" or "including" encompass the more restrictive terms "consisting essentially of" and "consisting of." For the purposes of the figures, like numerals are used to represent like or similar features between embodiments. It should also be understood that elements of one embodiment may be used with elements of another embodiment unless otherwise noted.

With specific reference to FIG. 1, an absorbent personal care article, specifically a feminine hygiene overnight pad 10, is shown in a top plan view. Overnight pads are often used by female adult consumers during their days of menstruation, so as to provide additional protection from staining their overnight clothing and bedding. Such overnight pads are often designed with extended lengths so as to provide coverage for the vaginal and buttocks area during sleep. Often such pads include a wider rear end area so as to thoroughly cover the buttocks region. The overnight pad 10 illustrated, is provided with a front end 11 and a rear end 12. The front end 11 is positioned towards a user's frontal pelvic area (in a user's undergarments) in use, and the rear end 12 is positioned towards a user's buttocks area, or rear pelvic area (in a user's undergarments) in use. Wings or flaps 13 are optionally positioned along the pad's longitudinal directed side edges 14 so as to secure such pad to the underside of a user's undergarments, via fasteners (not shown). A portion of the underside surface (not shown) of the wings typically includes the one or more fasteners. The fasteners will be selected to releasably engage either a garment or an overlapping portion of an opposed wing. Numerous adhesives and mechanical hook-type fasteners that releasably attach to itself or a user's garments are well known in the art and are suitable for use in connection with the present invention. Pressure sensitive adhesives are particularly well suited for use with the present invention. However, in order to protect the adhesive from contamination or drying prior to use, the adhesive is commonly protected by one or more releasable peel strips as is known in the art. A suitable releasable peel strip is a white Kraft paper having a silicone coating on one side so that it can be easily released from the adhesive. In addition, with respect to wing-to-wing attachment, examples of specific mechanical hook, adhesive and other fastening systems include but are not limited to those described in WO03/015682 to Hammonds et al.; WO03/015684 to Hammonds et al; and U.S. 20040133179 to Steger et al. each of which is hereby incorporated by reference in its entirety. The overnight pad 10 is illustrated with one set of wings 13, but can in alternative embodiments, include multiple sets of wings along the longitudinal side edges 14 as may be desired, to better accommodate the particular shape of the article and/or use on a particular style of garment. Any wings of such article can be constructed from materials described with respect to the topsheet and backsheet layers. In one embodiment, the wings can comprise an extension of a layer of material within the topsheet and/or backsheet layers. By way of example and in reference to FIG. 1, the wings 13 can be formed by an extension of the topsheet layer 20 and backsheet layer 30 that are welded together along edge seal 35. Such wings can be integrally formed with the main portion of the pad/absorbent article. Alternatively, the wings can be formed independently and separately attached to an inter mediate section of the article. Wings that are made independent of the other components of the absorbent article can be welded onto or adhesively joined to a portion of the topsheet and/or backsheet layers.

Alternatively, such a pad need not include wings, and may instead, rely on garment adhesive fasteners, as shown in FIG. 2A as 37, attached to the garment facing surface of a backsheet layer 30. As with any wing adhesive patches, the garment adhesive fasteners are desirably covered with a releasable peel strip 36. The use of garment adhesive on the backsheet layer 30 to help secure placement of an absorbent article on the garment is well known in the art and there are numerous adhesive patterns and releasable peel strips suitable for use with the present invention. Examples of suitable garment adhesives, patterns and release sheets include, but are not limited to, those described in U.S. Pat. No. 3,881,490 to Whitehead et al.; U.S. Pat. No. 3,913,580 Ginocchio; U.S. Pat. No. 4,337,772 to Roeder et al.; U.S. Pat. No. 4,556,146 to Swanson et al.; GB1349962 Roeder; and U.S. 20070073255A1 to Thomas et al. each of which is hereby incorporated by reference in its entirety.

The overnight pad 10 optionally, but desirably includes a liquid permeable, user-facing topsheet layer 20, a liquid impermeable, garment-facing backsheet layer 30 and at least one absorbent core layer 40 sandwiched between the topsheet layer 20 and the backsheet layer 30. At least one additional layer 50 is positioned between the absorbent layer 40 and the topsheet layer 20. In the illustrated embodiment of FIGS. 1 and 2A, two additional layers 50 and 60 are shown between the absorbent layer 40 and the topsheet layer 20. The additional layers may be either present in the form of a continuous planar base sheet 60, without material interruption, or as a discontinuous sheet 50, separated into discrete portions 50A, 50B spaced along the central longitudinal axis. It should be understood for purposes of this invention, that the additional layers which are separated into discrete portions and placed within the article, include a gap between the portions, in which the additional layer base sheet material is entirely absent. The gap is not the result of a formation hole or interstitial space formed during the initial, base sheet material layer extrusion or fiber laydown, but instead, the result of the additional layer being physically cut or otherwise separated into distinct sections or pieces, following initial layer creation (whether the additional layer of the base sheet being initially created via a foam, film, laminate, woven or nonwoven manufacturing process).

The overnight pad 10 has a lengthwise or longitudinal direction (axis) designated by line "L" and a widthwise or transverse direction (axis) designated by line "T". The longitudinal direction centerline (central longitudinal axis) of the pad 10 is shown as line "L c". Additionally, the pad includes a Z-direction (depth axis), which is noted in FIG. 2A (and other cross-sections) as line "Z". The overnight pad 10 (or other absorbent article of the invention) can comprise any one of numerous elongate shapes including, but not limited to, triangular, rectangular, dog-bone, "T"-shaped, and elliptical. In addition, it will often times be desirable for the pad to have rounded corners and/or generally convex ends.

The pad 10 desirably has in one embodiment, a length (along the central longitudinal axis) between about 80 mm and about 450 mm, and still more desirably a length between about 280 mm to about 420 mm for overnight pad configurations. The desired length will vary by the type of article and size of the user. The pad absorbent article 10 desirably has a maximum width along a transverse direction (excluding the wings) between about 60 and about 200 mm, and still more desirably a maximum width between about 75 mm and about 120 mm for overnight pad configurations.

As noted, the illustrated overnight pad 10 of FIGS. 1 and 2A has in the embodiment, two additional layers between the topsheet layer 20 and the absorbent core layer 40. These layers include a combination fluid guide, absorbent and shaping layer 50, and a printed, fluid surge layer 60. The fluid guide, absorbent and shaping layer 50 includes two portions 50A and 50B. The first portion 50A is configured to guide and absorb fluid from a user's vaginal opening, via a complete oval opening 52 in the first portion. The second portion 50B is configured to help shape the pad at (and create a close-to-body fit), and absorb fluid from a user's buttock's region. The two portions 50A, 50B are located desirably in on embodiment, in the same horizontal plane of the article, along the longitudinal direction, and are separated by a space or gap 54 (in which the base sheet material making up the additional layer 50 is completely absent across the transverse axis T) along the longitudinal central axis, such that the two portions are actually discrete/separated elements. While the two portions of the one layer 50 are initially manufactured from the same base sheet material, once they have been physically separated into distinct pieces, their different shape configurations and positions along the longitudinal axis provides the pad 10 with different functionality at two separate locations. The two portions 50A and 50B are manufactured from the same base sheet material, with the second portion 50B being cut or otherwise separated from the first portion 50A, and then placed at the desired location, spaced apart from the first portion 50A, but also along the central longitudinal axis of the article. Since the two portions are cut or otherwise separated from the same base sheet material, the chemical composition and physical components (fibers etc.) in the portions are generally the same, they being desirably made of a nonwoven formed base sheet. However, in one embodiment, such base sheet includes differential density along its length (as a result of zoned or patterned embossments), thereby providing the two resulting portions with different density ranges, depending on how they are separated, one from the confines of the other. In a further alternative embodiment, such base sheet material includes different colors in different regions, thereby resulting in the separate portions including different colors after separation. Use of the single base sheet material to produce two different physical features of the article results in reduction of waste material, without sacrificing desirable article attributes.

Of the two portions, the first portion 50A, closer to the front end 11 defines at least a partial opening 52 via an opening inner edge 53. In this particular embodiment, the first portion defines a complete opening in the shape of an oval. It should be understood that the shape of the opening 52 may vary by product type or design, and may be for example, a closed geometric shape such as circular, oval, rectangular or triangular. In such a configuration, the opening in the first portion 50A is surrounded on all sides (bounded on all sides) by base sheet material. For clarity purposes, the opening, or void space, passes between opposite sides of the planar base sheet material making up the first portion, and is surrounded by 360° of base sheet material in the X-Y plane. Alternatively the shape of the opening may be representative of a physical object, such as for example, the outer shape of a leaf, an animal, a star, a heart, a tear drop, a moon, the outer shape of a child's toy (such as a train) or even an abstract configuration. For such alternative shapes, the base sheet material of the first portion, still desirably in one embodiment, surrounds the opening on all sides in the X-Y plane. The first portion 50A, closer to the front end 11 of the pad, functions to absorb exudates via the material and to direct or guide fluid through the aperture/opening to the absorbent layer 40 beneath it in the Z direction. This feature permits a very rapid fluid acquisition into the pad 10, which can further reduce a feeling of rewet on the topsheet layer 20. This opening allows body fluids to be absorbed into a primary absorbent layer 40, without having to desorb fluid from a secondary absorbent layer above the primary absorbent layer 40. The void space or opening serves essentially as a channel to a lower layer (being bounded on all sides in the X-Y plane, by base sheet material). It also serves as a well to hold exudates while it is absorbed into the absorbent layer 40.

For feminine care absorbent articles the following dimensions are desirable. Desirably the width of the first portion 50A, along the transverse direction of the product is between about 20 mm and 100 mm, more desirably between about 30 mm and 80 mm. Desirably the length of the first portion 50A, along the longitudinal direction of the product, is between about 30 mm and 300 mm, more desirably between about 50 and 150 mm. Desirably the opening in the first portion 50A is selected from an oval or circular shape, having between about 100 $mm^2$ and 4100 $mm^2$ area, in one embodiment between about 100 $mm^2$ and 1000 $mm^2$ area, and in another embodiment between about 450 $mm^2$ and 4100 $mm^2$ area. It is desirable that the opening be large enough for a consumer to easily view and place it directly under her vaginal opening, in the case of a feminine hygiene absorbent article, or under a genital opening or anal opening in the case of other absorbent article types. For other types of absorbent articles, this placement may vary. It is desirable in one embodiment for the first portion area, excluding the opening, to be between about 800 $mm^2$ and 30,000 $mm^2$.

The first portion includes a front end facing edge 55 and a rear end facing edge 56. In one embodiment, it is desirable for the first portion, front end facing edge 55 to be from between about 15 mm to 150 mm from the pad front end 11. In one embodiment, the length dimension of the absorbent article can be divided into thirds, and the first portion is located at least partially in the front end most-directed third of the article. It is desirable for the second portion (in a two portion configuration) to be located at least partially in the back end directed third of the absorbent article length. In one embodiment, the first portion and the second portion have the same height/thickness along the Z direction.

The second portion 50B includes a front end facing edge 57 and a rear end facing edge 58. The second portion 50B is closer to the pad rear end 12 than the first portion 50A and is also aligned on the longitudinal central axis Lc of the pad 10. It is spaced apart 54 from the first portion at a sufficient distance so as to align it under a user's buttocks region when in use. The two portions are discrete from one another within the article, but were originally formed from the same base sheet material, since the second portion 50B was desirably cut from within the confines of the first portion 50A.

Desirably, in one feminine hygiene pad embodiment, the space or gap 54 between the first portion 50A rear end facing edge 56 and the second portion front end facing edge 57 is between about 10 mm and 250 mm, more desirably between about 40 mm and 150 mm.

Since the second portion 50B is completely removed, cut, punched out, or otherwise cleanly separated from the first portion 50A, its shape can be considered a mate of and is complementary to the shape of the opening 52 of the first portion. Its shape can fit in, or is mated such that it could fit precisely within the opening 52 of the first portion 50A. The structure of the first portion 50A defines an inner edge 53 and the portion of base sheet material that is removed from the first portion defines a second portion (external) periphery edge 59. The inner and external edges could be considered of such similarity, that one edge is capable of fitting neatly within or adjacent the other/or even that one has an edge that is concentric with the other. Therefore in an alternative embodiment, such an absorbent article includes an additional layer having at least two portions, with the two portions including complementary edges. In one embodiment, the complementary edges include a first portion inner edge and a second portion peripheral edge. As an alternative to the invention, one or more of the portions which are cut from each other, may be cut with a beveled edge to provide for a more gradual incline in the portion structures.

The second portion, depending on embodiment, may entirely fit within the first portion (for complete openings in the first portion), or alternatively, may only partially fit within the first portion (for partial openings in the first portion). Essentially, the additional layers that are separated into portions, include mated elements that are positioned along the central longitudinal axis, with at least some areas of the portion structures capable of fitting precisely within each other.

Desirably in one embodiment, the area of the second portion, that is cutout from or otherwise removed to create the opening in the first portion, is between about 450 $mm^2$ and 4100 $mm.^2$ In a further embodiment, it is desirable for the width of the second portion in the transverse direction, to be between about 15 mm and 50 mm, the length of the second portion along the longitudinal direction, to be between about 30 mm and 80 mm, and for the rear end facing edge 58 of the second portion 50B to be between about 15 mm and 75 mm from the rear end 12.

Desirably, in one embodiment, the portions serve nonabsorbent functions, and are designed rather to provide shaping, stabilizing (restriction of article movement or article rigidifying purposes), or fluid guiding functions or a combination thereof. Alternatively, such portions provide absorbency functionality, or absorbency in addition to the foregoing nonabsorbent functions. The portions therefore may serve as an additional absorbent layer, in addition to the primary absorbent layer 40. Still further layers may be included adjacent the discrete portions, either between the portions and the topsheet layer 20, between the portions and the absorbent layer 40, or between the discrete portions themselves (such that the portions are on separate horizontal planes within the article).

As an example, the second additional layer 60, the continuous additional layer shown in the embodiment of FIGS. 1 and 2A (and in other embodiments) and situated between the topsheet layer 20 and the absorbent layer 40, is a fluid surge layer, designed to handle rapid surges of fluid into the pad 10. Such a layer is optional and may number more than one. Desirably in one embodiment, such surge layer is printed with an image, in this case a series of circles or dots 62, such that a consumer can see such lower surge layer through a translucent or partially translucent topsheet layer, it being visible from the bottom of the oval opening 52. It should be understood that any printed pattern or solid color surge layer may be used to achieve this purpose. Such printing of a layer 60 beneath the first portion 50A would highlight the portion feature with opening, in the article. Such surge layer may be of a shortened lengthwise dimension so as to be dimensioned to exactly match the length and width dimensions of the first portion 50A, as illustrated in FIG. 2A, or alternatively of a longer dimension as seen in FIG. 2B. Alternatively, such printed surge layer may be dimensioned to merely match the dimensions of the opening 52.

In an alternative embodiment, the absorbent layer 40 may itself be printed or colored to highlight the opening in the first portion 50A, without use of a printed surge, or in addition to the use of an unprinted surge layer. Such printing or coloration could similarly be readily visible through the topsheet layer 20 (and surge layer if present) by a user in one embodiment. Alternatively, the first and second portions themselves 50A, 50B may be colored or printed to accomplish the same objective, and could be similarly visible through the topsheet layer 20 by a user. In a further alternative embodiment, the portions may be of a first color and the surge layer may be of a second color or print pattern.

As indicated, the placement of the various portions described, will be determined by the product type and user size. For example, if a first portion is designed to capture urine, rather than menses, it may be placed at a different distance from a second portion, which may be alternatively designed to capture feces. In the case of a feminine hygiene article, both features may be designed to capture menses exudates, the first portion designed to capture exudate directly off of the vaginal opening, the second portion designed to capture any menses exudates that may flow between the buttocks of a user during sleep. Alternatively, the portion locations may be reversed, such that a portion with opening is situated towards the rear end of an article and a hump-like portion is situated towards a front end of an article.

It should be recognized that each of the various layers of an absorbent article of the invention are desirably bonded either directly or indirectly to adjacent layers in the Z-direction, of the article. Such bonding techniques are conventional in the field of consumer absorbent products, and are not illustrated in the exploded views. However, for example such methods include adhesive, ultrasonic, and thermal bonding. Specifically, construction adhesive, can in one embodiment secure each layer to adjacent layers within the Z-direction of the article. Such adhesive may be applied via a continuous coating or spray, or a discontinuous coating or spray. In some embodiments, it may not be necessary to apply adhesive to each internally facing surface of each layer within an article. A combination of bonding techniques can also be used, such as the use of thermal bonding or ultrasonic bonding for the article peripheral edges 35 and adhesive bonding for internal layers.

Figure 2C:
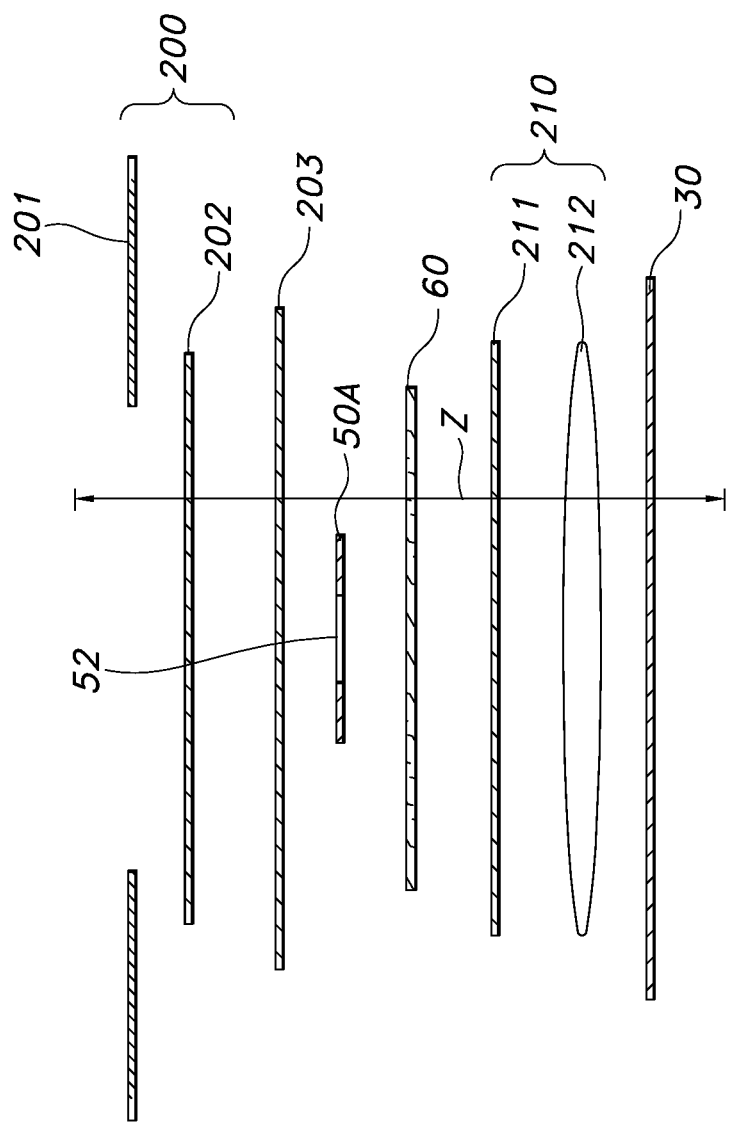
FIG. 2C is a cross-sectional, exploded view of the alternative embodiment of the feminine hygiene overnight pad of FIG. 1 (as seen in FIG. 2B), taken along a transverse axis through the first portion, at lines 2C-2C.

In an alternative embodiment of the feminine hygiene overnight pad of FIGS. 1 and 2A, an alternative multi-layered construction is shown in two different cross-sectional, exploded views, along lines 2B-2B and 2C-2C of FIG. 1, in FIGS. 2B and 2C. The views show a central longitudinal axis, cross-sectional exploded view and a transverse axis, cross-sectional exploded view respectively. In such embodiment, a two-layered topsheet layer (also known as a dual cover or bicomponent cover) 200 is present having a user-facing nonwoven topsheet material 201 at the article lateral edges (seen in FIG. 2C), and a center apertured film topsheet material 202. A second surge layer 203 is present adjacent the film topsheet layer 202, between the topsheet layer 200 and the first and second portions 50A and 50B. A printed surge layer 60 is situated beneath the portions 50A and 50B, such that a printed pattern can also be seen in this alternative embodiment through the topsheet layer 200. Immediately adjacent the printed surge layer 60, and beneath it in the Z direction, is situated a multiple-layered absorbent core 210 comprised of an upper airlaid layer 211 and lower tissue-wrapped, superabsorbent and fluff composite 212. As with the previous embodiment, a backsheet layer 30 is present to serve as a garment-facing layer and garment-protecting liquid impermeable surface. It should be understood that the absorbent layer may be formed from a variety of structures, such as for example fluff layers, multicomponent laminates, superabsorbent containing sheets, nonwoven materials or combinations thereof.

Figure 2D:
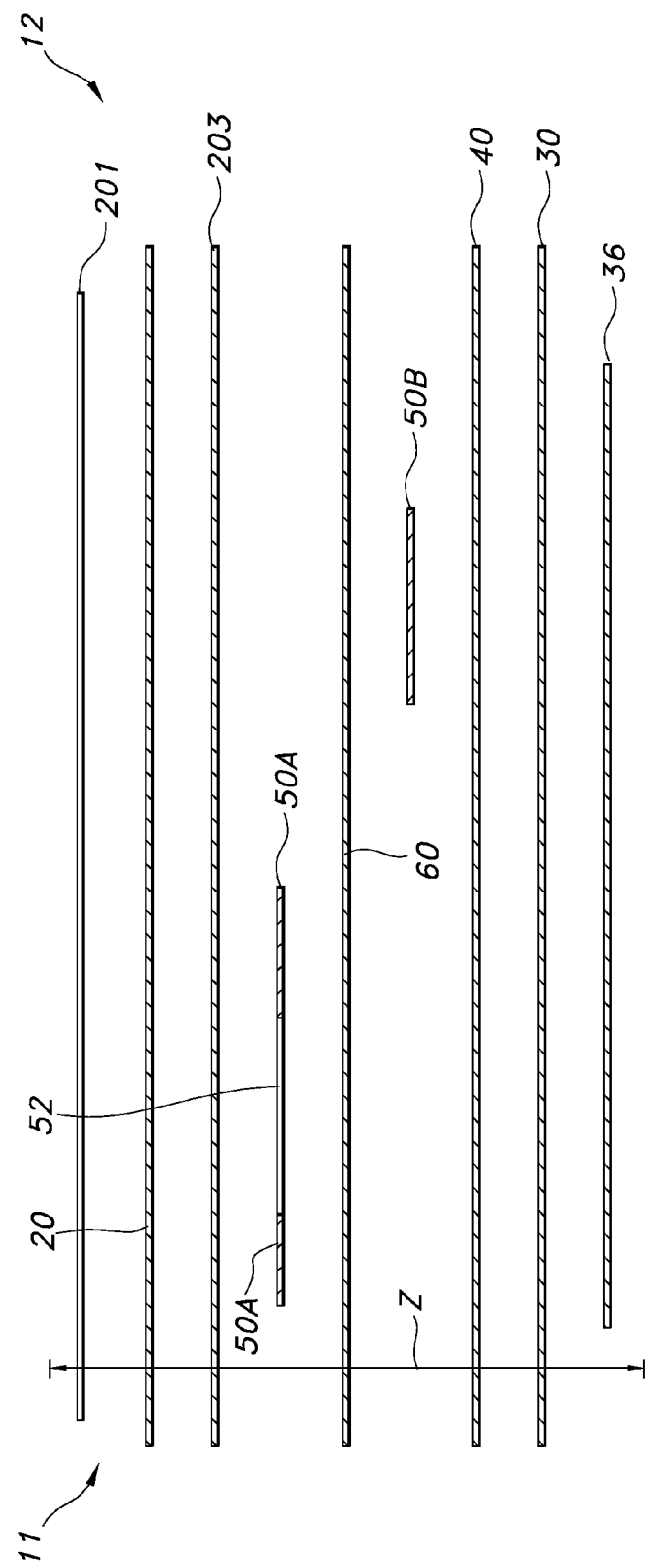
FIG. 2D is a cross-sectional, exploded view of an alternative embodiment of the feminine hygiene overnight pad of FIG. 1 taken along lines 2D-2D, approximately at the central longitudinal axis.

In an alternative embodiment of FIG. 1, as shown in the cross-sectional, exploded view of FIG. 2D, taken along the lines 2D-2D of FIG. 1 (generally along the longitudinal central axis), the two portions 50A and 50B of the additional layer are placed in different horizontal planes within the pad, rather than in the same horizontal plane. As can be seen, the two portions are separated by a surge layer 60 in FIG. 2D, rather than being placed on the same side of the surge layer 60. Still, within this embodiment, both portions of the additional layer are placed either directly upon, or indirectly upon the absorbent layer 40.

Figure 2E:
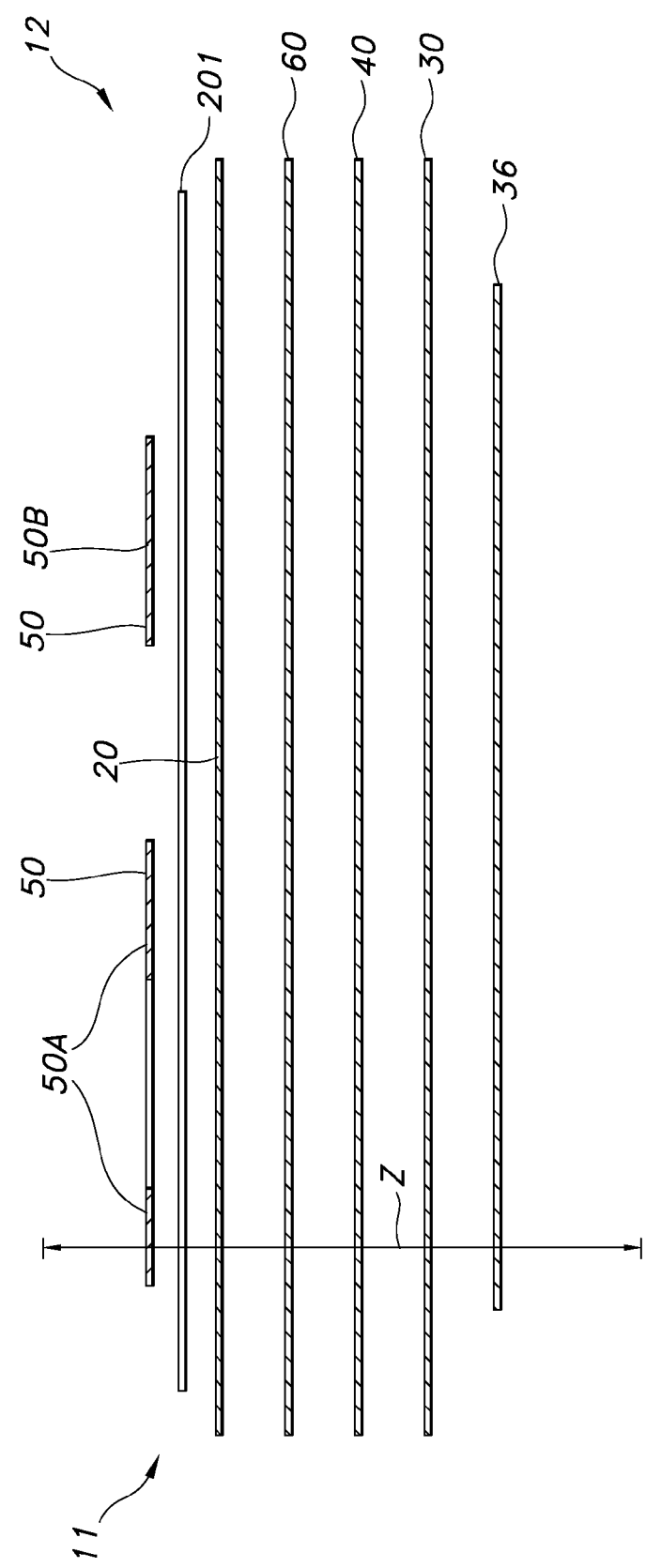
FIG. 2E is a cross-sectional, exploded view of a further alternative embodiment of the feminine hygiene overnight pad of FIG. 1 taken along lines 2E-2E, approximately at the central longitudinal axis.

As shown in cross-sectional, exploded view of FIG. 2E, taken along the lines 2E-2E of FIG. 1 (generally along the longitudinal central axis), the two portions 50A and 50B are placed upon a dual cover topsheet layer 20 (with lateral side pieces 201), rather than beneath it in the Z-direction. In such embodiment, in which the portions would be bonded either directly to the user-facing surface of the topsheet layer 20 (central portion) or layers beneath the topsheet layer, a user of the pad would be clearly able to see the portions of the additional layer 50 for placement in anatomically desired locations.

Figure 2F:
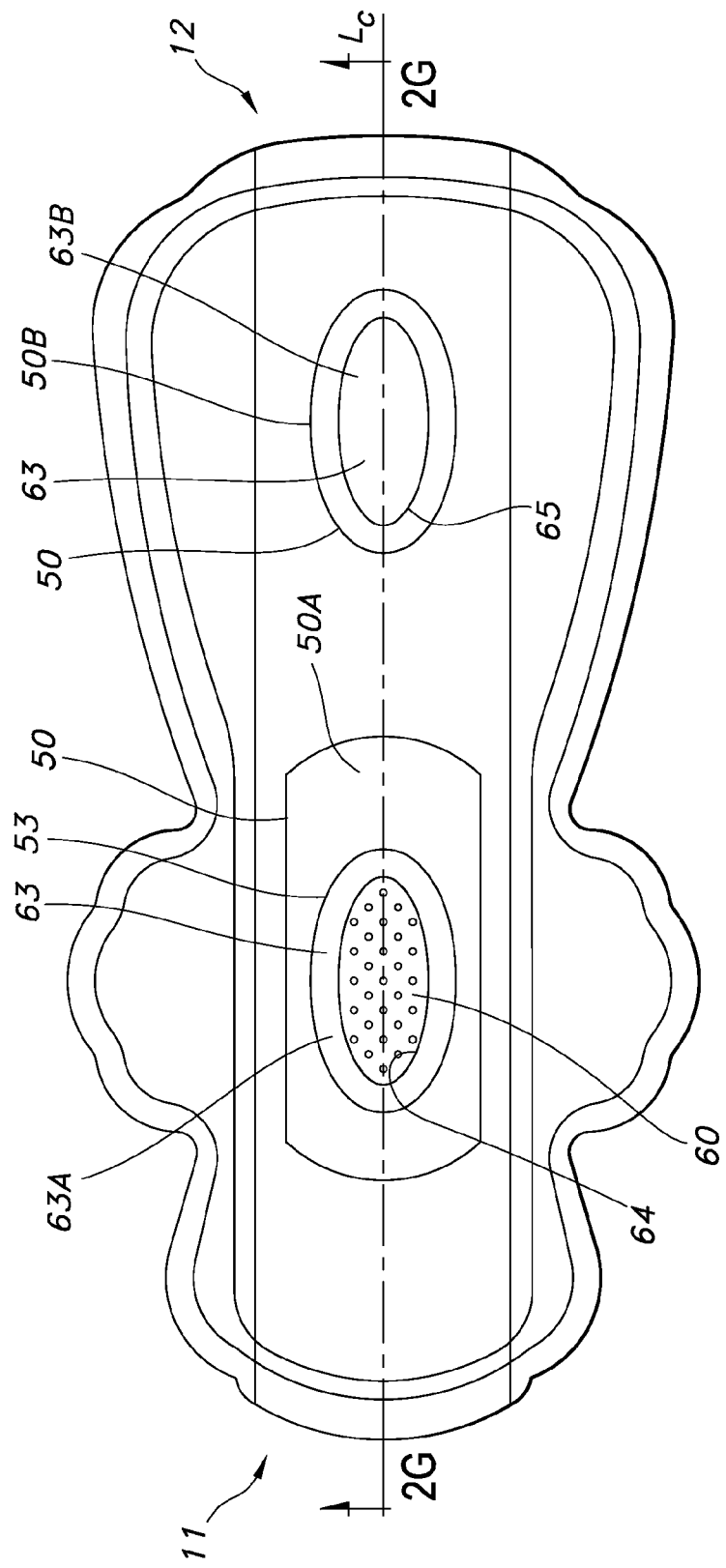
FIG. 2F is a top plan view of a further alternative embodiment of the feminine hygiene overnight pad of FIG. 1.
Figure 2G:
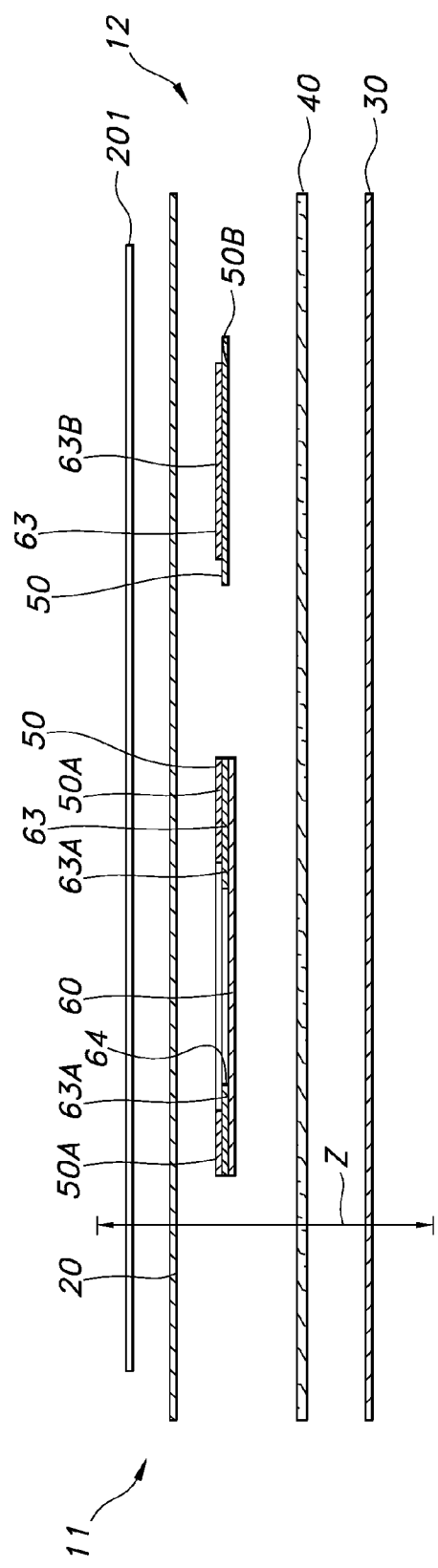
FIG. 2G is a cross-sectional, exploded view of the further alternative embodiment of the feminine hygiene overnight pad of FIG. 2F taken along lines 2G-2G, approximately at the central longitudinal axis.

In still yet a further alternative embodiment of the invention, a top plan view and respective central longitudinal axis cross-sectional, exploded view along lines 2G-2G, of a feminine hygiene overnight pad is shown in FIGS. 2F and 2G. As can be seen in these figures (which also illustrate a dual cover feature), instead of having only one set of discrete portions derived from one additional layer, several additional layers 50, 63 may be employed, one atop the other in the Z-direction. In this fashion, a funnel-like effect can be created using the first portions 50A, 63A of the additional layers, and a raised hump feature can be enhanced using the second portions 50B, 63B of the additional layers. The stepped, funnel-like structure made from the progressively smaller cut first portions, would further enhance the channeling of fluid to the lower absorbent layer 40. In this embodiment, the smaller cut, first portion 63A would define an inner edge 64 that could be seen beyond the larger cut, first portion 50A inner edge 53. The raised cut-out sections 50B, 63B would enhance the close-to-body fit feature of the hump, as progressively smaller cut-outs are placed one atop the other towards the topsheet layer, in the Z direction. As with previous embodiments, a printed surge layer 60 can be visible through the topsheet from above the absorbent layer 40. It should be recognized that while the second portion hump-like features are shown with the smaller oval cutout atop the larger oval cutout, the reverse order of cutouts may also be employed. A similar reversal of placement order could also be employed for the first portions, so as to create a somewhat enclosed, well-like feature.

Figure 3:
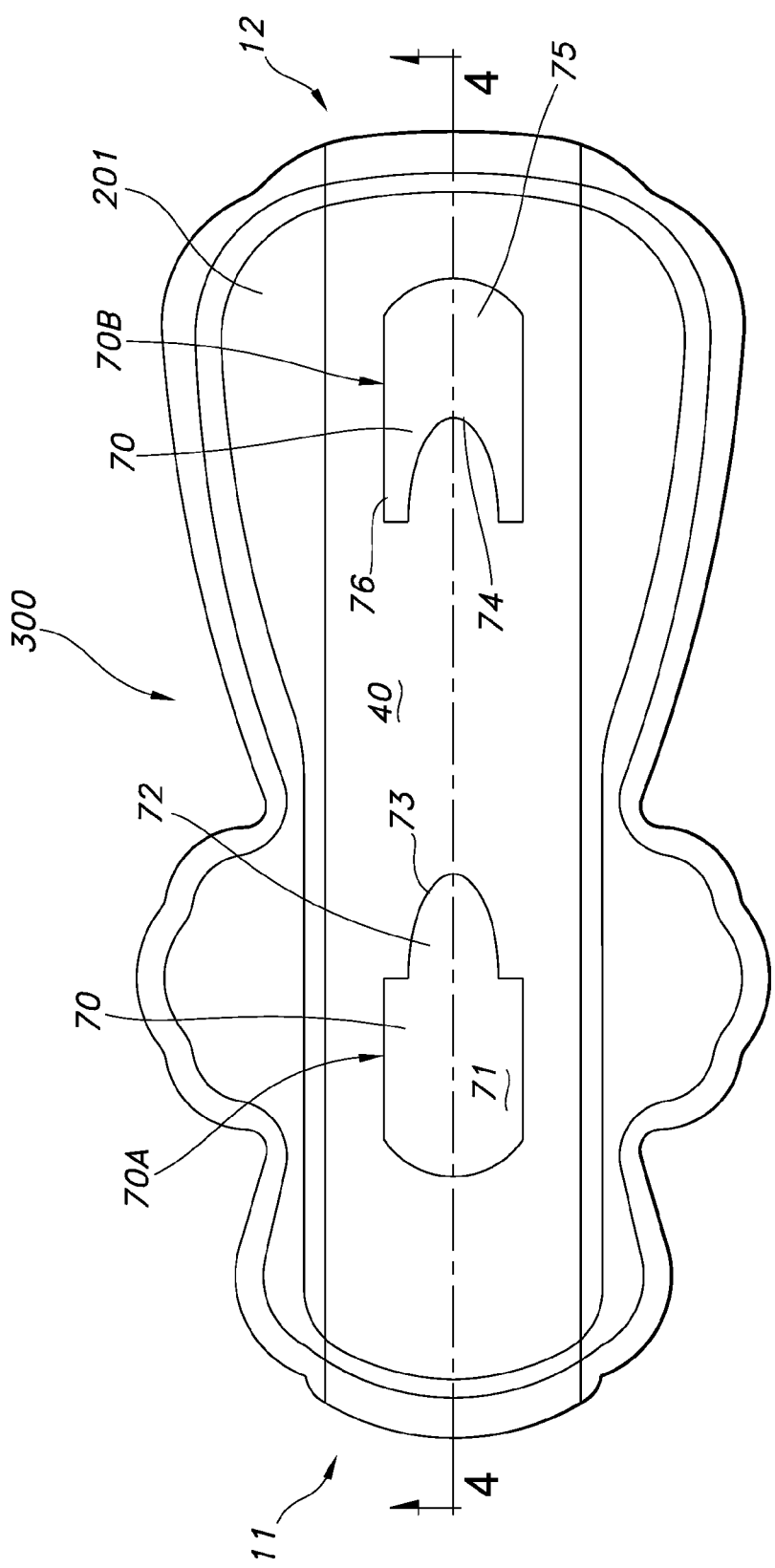
FIG. 3 is a top plan view of an alternative embodiment of an absorbent article of the present invention, also in the form of a feminine hygiene overnight pad, in a flat and unfolded state.
Figure 4:
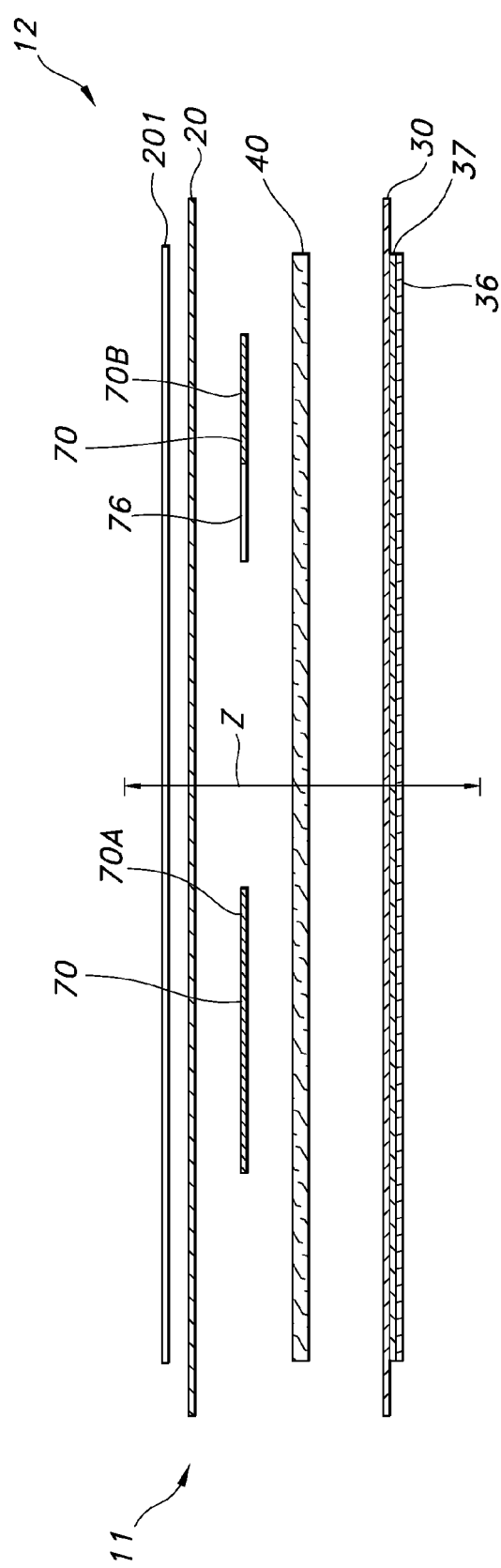
FIG. 4 is a cross-sectional, exploded view of the feminine hygiene overnight pad of FIG. 3 taken along lines 4-4 (along the longitudinal central axis).

In still a further alternative embodiment of a feminine hygiene overnight pad in accordance with the invention, a top plan view and central longitudinal axis, cross-sectional exploded view along lines 4-4 of the alternative embodiment is illustrated respectively in FIGS. 3 and 4. As can be seen in the figures, a feminine hygiene overnight pad 300 includes a topsheet layer 20, a backsheet layer 30 and an absorbent layer 40 sandwiched therebetween, as in the previous embodiments. An additional layer 70 is placed between the topsheet layer 20 and the absorbent layer 40. The additional layer 70 is comprised of two portions 70A and 70B that are formed from one base sheet material, and then cut and placed as separated and discrete elements along the central longitudinal axis of the pad, and within the same horizontal plane of the pad. However, as can be seen in the figures, the portion facing the front end in this alternative embodiment does not define a partial or complete opening. Rather, the portion 70A includes a generally rectangular region 71 and a protruding region or section 72 having a convex outer edge 73 (periphery edge) facing the rear end of the pad 12. The second portion 70B includes a solid region 75 that further defines a partial opening by extensions 76, including a concave edge 74 (periphery edge). Since the two portions 70A, 70B have been cut from the same base sheet material, the edges 73 and 74 are matched and the defined shapes are complementary, with the portions mated such that the first portion 70A can partially fit within the second portion 70B. The periphery edges of these portions are complementary. In this fashion, two topographical features can be added to a pad with one providing a partial opening for directing fluid to the absorbent layer 40 located beneath it in the Z direction. The two layers are of the same chemical composition and demonstrate the same physical make-up. It should be noted that in one embodiment, such partial opening is surrounded by base sheet material from between above 180°, to less than 360° in the X-Y plane. In still a further embodiment, such partial opening is surrounded by base sheet material at between about 270° to less than 360° in the X-Y plane. Such partial openings (even though open towards the front end side, along the longitudinal direction) still serve as a channel bounded in part by base sheet material 75,76, and directing the flow of fluid exudates to a lower absorbent layer 40.

Therefore, in an alternative of the absorbent article, the shape of the at least partial opening of a first portion, is complementary to the shape of the second portion. In yet another alternative of the absorbent article, the shape of the complete opening of the first portion is complementary to the shape of the second portion. In still a further alternative of the absorbent article, the shape of the at least partial opening of the first portion is complementary to the shape of a section or region of the second portion. In still a further alternative embodiment, the shapes of the portions of the additional layer are complementary. In still a further alternative embodiment, the additional layer includes two or more portions having complementary edges, with the complementary edges from the two portions being periphery edges of the respective portions.

Figure 5:
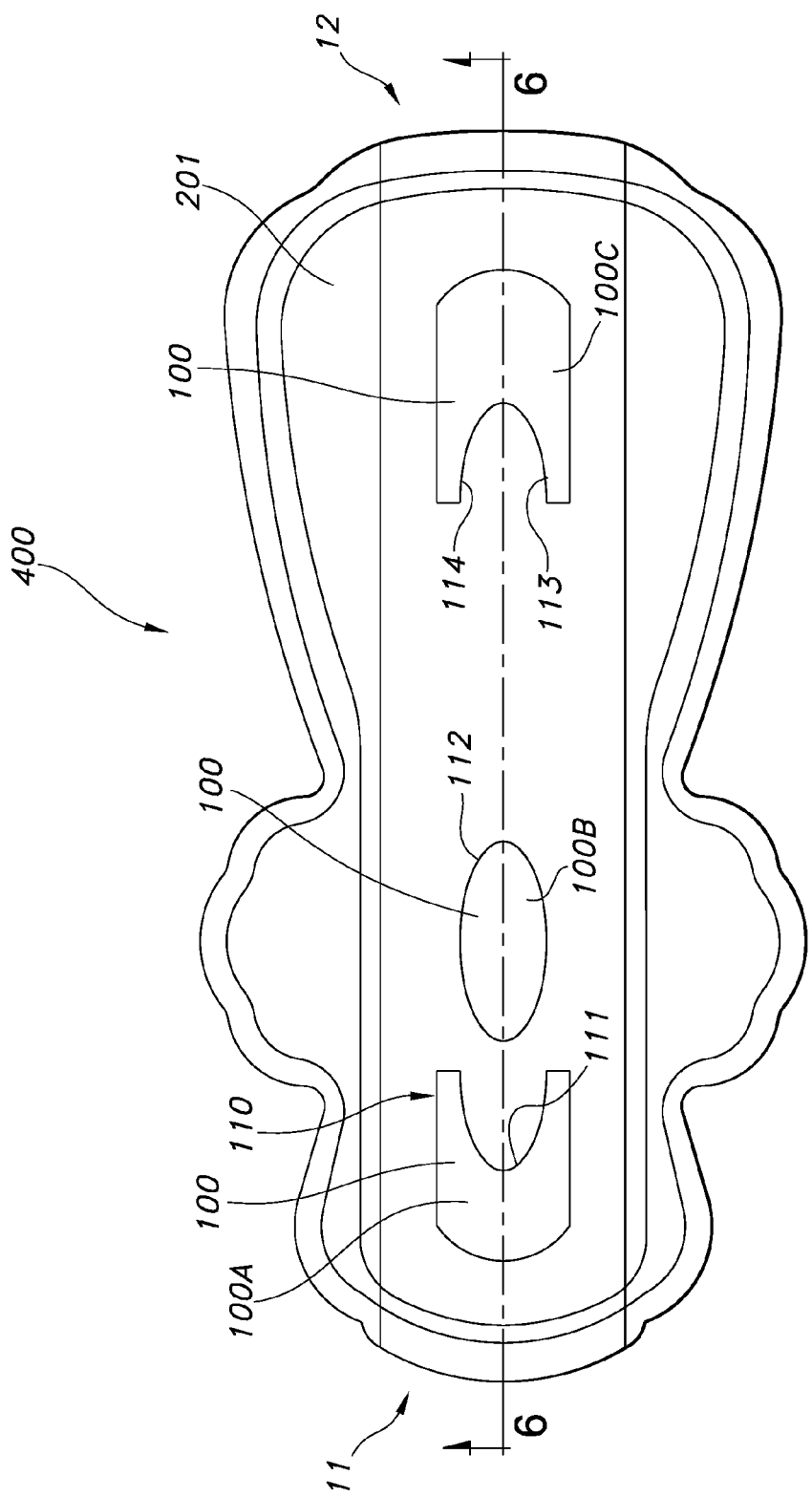
FIG. 5 is a top plan view of an alternative embodiment of an absorbent article of the present invention, also in the form of a feminine hygiene overnight pad, in a flat and unfolded state.
Figure 6:
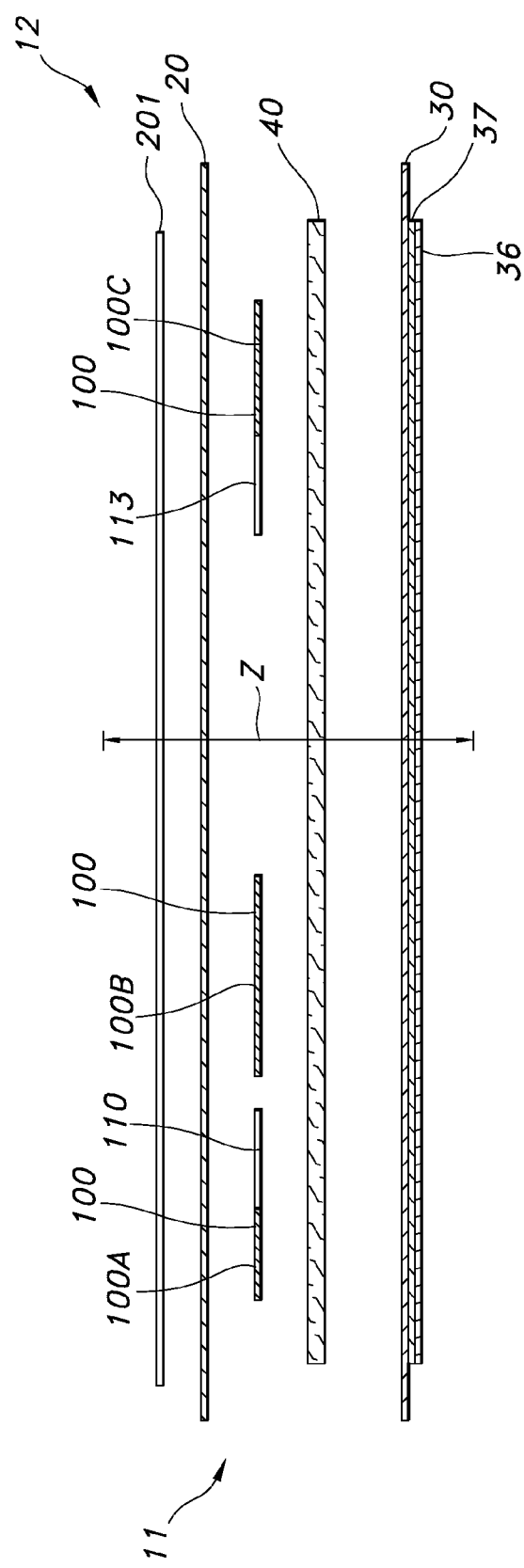
FIG. 6 is a cross-sectional, exploded view of the feminine hygiene overnight pad of FIG. 5 taken along lines 6-6 (along the longitudinal central axis).

In still another alternative embodiment of a feminine hygiene overnight pad in accordance with the invention, a top plan view and central longitudinal axis, cross-sectional exploded view along lines 6-6 of the alternative embodiment is illustrated in FIGS. 5 and 6. As can be seen in the figures, a feminine hygiene overnight pad 400 includes a topsheet layer 20, a backsheet layer 30 and an absorbent layer 40 sandwiched therebetween, as in the previous embodiments. An additional layer 100 having three portions is placed between the topsheet layer 20 and the absorbent layer 40. The additional layer 100 is comprised of three portions 100A, 100B and 100C that are formed from one base sheet material, and then cut and placed as separated and discrete elements along the central longitudinal axis of the pad, and within the same horizontal plane of the pad. However, as can be seen in the figures, the portion 100A facing the front end 11 in this alternative embodiment defines a partial opening 110 formed by concave edge 111. The second portion 100B is in the shape of an oval and includes an outer edge 112. The second portion 100B is situated between, but separated from the first portion 100A and the third portion 100C. The size of the gaps between the portions may be varied to suit the needs of the absorbent article. The third portion 100C is situated towards the rear end of the pad 12 and defines a partial opening 113 including a concave edge 114. Each of the three portions thereby have matched or complementary edges with at least one other portion, and in one case (for the second portion) with two other portions. In this fashion, three topographical features can be added to a pad, with two portions defining partial openings for directing fluid to the absorbent layer 40 located beneath them in the Z direction. Essentially, this embodiment includes first and second portions having shapes (and edges) that are each complementary only with a third portion shape (and edge), the third portion shape being complementary (in shape and edges) to both the first and second portion shapes (and edges).

It should be recognized that the number of portions of the additional layer(s) can be varied by product type and size. In an alternative embodiment the length dimension of the absorbent article can be divided into thirds, and the first portion is located at least partially in the front end most directed third of the article. It is desirable for the second or middle portion (in a three portion configuration) to be located at least partially in the middle third of the article and the third portion to be located at least partially in the back end-directed third of the absorbent article. In one embodiment, the first, second and third portions have the same height/thickness in the Z direction.

Figure 7:
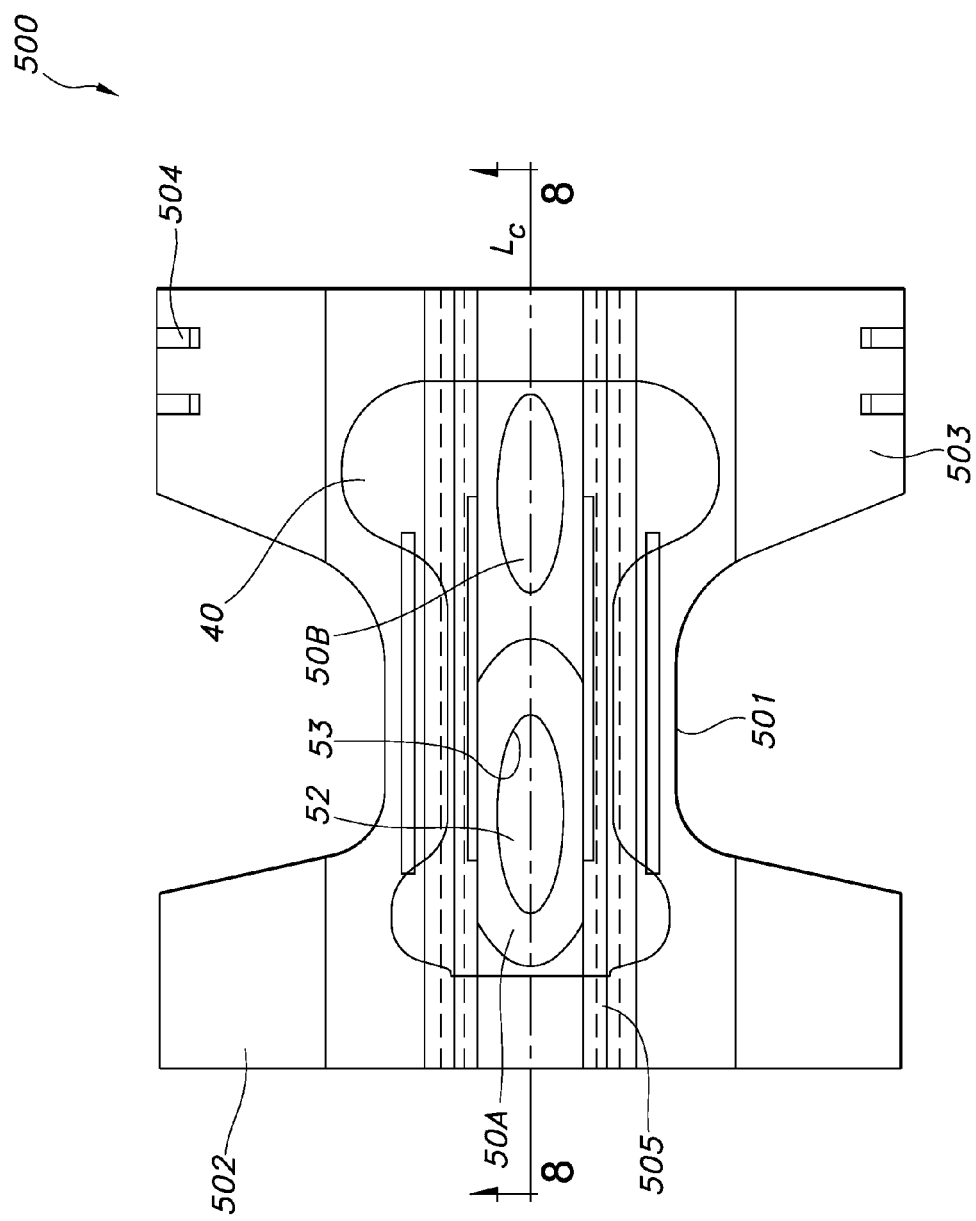
FIG. 7 is a top plan view of an alternative embodiment of an absorbent article of the invention, in the form of a diaper.
Figure 8:
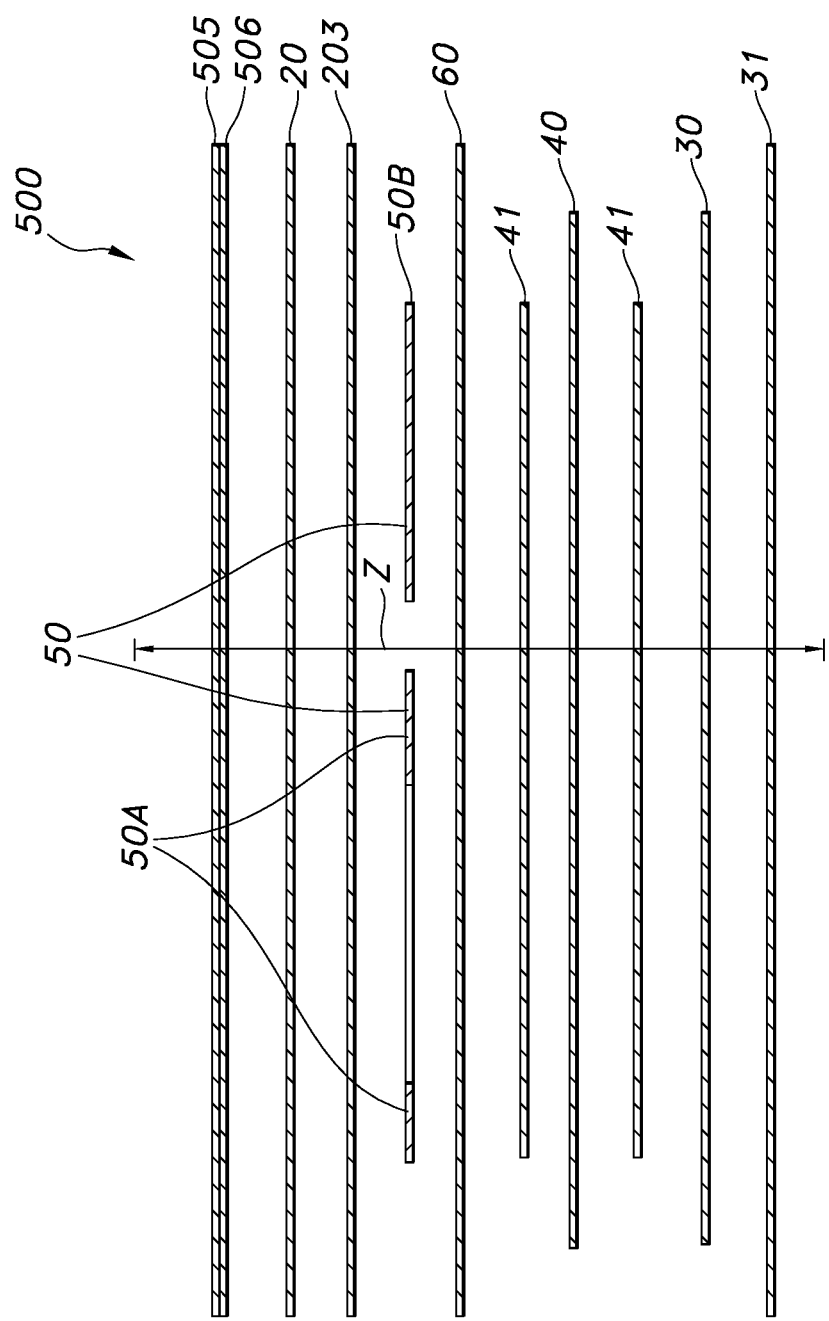
FIG. 8 is a cross-sectional, exploded view along the central longitudinal axis, along lines 8-8, of the diaper of FIG. 7.

In yet another embodiment of the invention, as can be seen in FIG. 7, which illustrates a top plan view of a diaper, a baby's, child's or adult care diaper 500 is shown that includes a central crotch region 501, a first waist region 502 and a second waist region 503 including fasteners 504. The diaper 500 includes a central longitudinal axis Lc, as with previously described embodiments. The diaper includes a topsheet layer 20, and a backsheet layer 30 which sandwich an absorbent layer 40. Conventional bowel movement-containing flaps 505, with embedded elastic components 506 are positioned upon the liner 20 layer to face a user. Such flaps are designed to provide sealed engagement between the diaper and a user's crotch region for capturing body exudates. As with previous embodiments, several additional layers are included within the diaper layered structure, including, an extra nonwoven backsheet layer 31 for providing a pleasant feel to the backsheet 30, two tissue layers 41 for wrapping the absorbent layer 40, and two surge layers 60 and 203. An additional layer 50 includes two portions 50A, 50B positioned upon the absorbent layer 40, a first portion 50A, for directing exudates down to the absorbent layer 40 in the Z direction through an opening 52 defined by inner opening edge 53. As with previous embodiments shown in FIGS. 1, 2A, 2B, 2C, 2D, and 2E, the base sheet material in the first portion 50A of the diaper, defines a complete opening or aperture, rather than a partial opening.

For diaper product configurations the following dimensions are desirable. Desirably the width of the first portion 50A, along the transverse direction of the product is between about 20 mm and 190 mm, more desirably between about, 50 mm and 190 mm, still more desirably between about 80 mm and 180 mm, depending on diaper end use. Desirably the length of the first portion 50A, along the longitudinal direction of the product, is between about 40 mm and 600 mm, more desirably between about 100 mm and 300 mm. Desirably the opening in the first portion 50A is selected from an oval or circular shape, having between about 1800 $mm^2$ and 30000 $mm^2$ area, in one embodiment. It is desirable that the opening be large enough for a consumer to easily place it directly under their genital or anal opening. It is desirable in one embodiment for the first portion area, excluding the opening, to be between about 4000 mm² and 114000 mm². It is desirable for the distance from the front end facing edge of the first portion to be between about 110 mm and 300 mm from the front end of the diaper. It is further desirable in one embodiment, for the first portion rear end edge and the second portion front end edge to be separated by a gap of between about 10 mm and 300 mm, more desirably between about 50 mm and 190 mm. It is further desirable for the second portion to have a width in the transverse direction of between about 15 mm and 100 mm, alternatively between about 30 mm and 100 mm, and a length in the longitudinal direction of between about 30 mm and 300 mm, alternatively between about 60 mm and 300 mm. In one embodiment, the area of the second portion is between about 1800 mm² and 30000 mm.²

With respect to the general function and composition of the overnight pad absorbent articles described herein, the backsheet layer 30 specifically functions to isolate absorbed fluids from the wearer's garments and therefore comprises a liquid-impervious material. In one aspect, the backsheet layer 30 may optionally comprise a material that prevents the passage of liquids but allows air and water-vapor to pass there through. The backsheet layer 30 can comprise a single layer or multiple layers and these one or more layers can themselves comprise similar or different materials. Suitable backsheet layer materials include, but are not limited to, polyolefin films, nonwovens and film/nonwoven laminates. The particular structure and composition of the backsheet layer 30 may be selected from various known films and/or fabrics with the particular material being selected as appropriate to provide the desired level of liquid barrier, strength, abrasion resistance, tactile properties, aesthetics and so forth. Suitable backsheet layers include, but are not limited to, those described in U.S. Pat. No. 4,578,069 to Whitehead et al.; U.S. Pat. No. 4,376,799 to Tusim et al.; U.S. Pat. No. 5,695,849 to Shawver et al; U.S. Pat. No. 6,075,179 et al. to McCormack et al. and U.S. Pat. No. 6,376,095 to Cheung et al. each of which is hereby incorporated by reference thereto in its entirety.

The optional topsheet layer 20 functions to receive and take in fluids, such as urine or menses, and therefore comprises a liquid permeable material. Additionally, topsheets can further function to help isolate the wearer's skin from fluids held in the absorbent core layer 40. If present, topsheet layers can comprise a single layer or multiple layers and these one or more layers can themselves comprise similar or different materials. Topsheet layers are well known in the art and may be manufactured from a wide variety of materials such as, for example, porous foams, reticulated foams, apertured plastic films, woven materials, nonwoven webs, apertured nonwoven webs and laminates thereof. It is also well known that one or more chemical treatments can be applied to the topsheet layer materials in order to improve movement of the fluid through the topsheet and into the article. Furthermore, topsheet layers can include "dual cover" or bicomponent constructions, in which a first material is positioned along the longitudinally directed center line of a product and secondary materials are positioned along the longitudinal side edges of a product. Such a dual cover construction would allow for different functionality at the regions associated with immediate fluid deposition and those regions in contact with a user's legs. Suitable topsheet materials and constructions include, but are not limited to, those described in U.S. Pat. No. 4,397,644 to Matthews et al.; U.S. Pat. No. 4,629,643 to Curro et al.; U.S. Pat. No. 5,188,625 Van Iten et al.; U.S. Pat. No. 5,382,400 to Pike et al.; U.S. Pat. No. 5,533,991 to Kirby et al.; U.S. Pat. No. 5,415,640 to Kirby; U.S. Pat. No. 5,961,505 to Coe; U.S. Pat. No. 6,117,523 to Sugahara; and U.S. Pat. No. 6,410,823 to Daley et al.; each of which are hereby incorporated by reference thereto in its entirety.

Between the liquid pervious topsheet layer 20 and liquid impervious backsheet layer 30 is positioned at least one absorbent core layer 40. The absorbent layer 40 (also known as the absorbent core or core layer) functions to absorb and preferably "lock-up" the bodily fluids that pass into the overnight pad absorbent article 10 through the topsheet layer 20. The absorbent core layer 40 can comprise a single layer or multiple layers and these one or more layers can themselves comprise similar or different materials. In order to efficiently and effectively utilize the absorbent capacity of the article, it is common for the absorbent core to include one or more liquid distribution layers or wicking layers in combination with a highly absorbent layer that preferentially absorbs and retains the liquids. Suitable wicking layers include, but are not limited to, bonded-carded webs, hydroentangled nonwoven webs, or spunbond webs containing fibers treated with or containing one or more topical agents that improve the contact angle with the bodily fluid and/or modify the flow properties of the bodily fluid. Highly absorbent layers often include, but not limited to, batts or webs containing wood pulp fibers, superabsorbent particles, synthetic wood pulp fibers, synthetic fibers and combinations thereof. Such highly absorbent layers may be themselves further wrapped in nonwoven sheet materials, such as for example, polymeric nonwoven layers such as spunbond, meltblown or laminates thereof, or alternatively natural fiber nonwoven layers such as tissue. The absorbent core may comprise any one of a number of materials and structures, the particular selection of which will vary with the desired loading capacity, flexibility, body fluid to be absorbed and other factors known to those skilled in the art. By way of example, suitable materials and/or structures for the absorbent core include, but are not limited to, those described in U.S. Pat. No. 4,610,678 to Weisman et al.; U.S. Pat. No. 6,060,636 to Yahiaoui et al.; U.S. Pat. No. 6,610,903 to Latimer et al.; U.S. Pat. No. 20100174260 to Di Luccio et al.; and U.S. Pat. No. 7,358,282 to Krueger et al.

The shape of the absorbent core layer 40 can vary as desired and can comprise any one of various shapes including, but not limited to, generally triangular, rectangular, dog-bone, "T"-shaped, and elliptical shapes. In one embodiment, the absorbent core layer 40 has a shape that generally corresponds with the overall shape of the overnight pad absorbent article 10 such that the absorbent core terminates 41 proximate the edge seal 35 and wings 13. The dimensions of the absorbent core layer 40 can be substantially similar to those referenced above with respect to the pad 10; however it will be appreciated that the dimensions of the absorbent core layer 40 while similar, will often be slightly less than those of the overall pad 10 in order to be contained therein.

As previously indicated, the absorbent core layer 40 is positioned between the topsheet layer 20 and backsheet layer 30. The individual layers comprising the article can be attached to one another using means known in the art such as adhesive, heat/pressure bonding, ultrasonic bonding and other suitable mechanical attachments. Commercially available construction adhesives usable in the present invention include, for example Rextac adhesives available from Huntsman Polymers of Houston, Tex., as well as adhesives available from Bostik Findley, Inc., of Wauwatosa, Wis. In one embodiment, and in reference to FIG. 1, the absorbent core can be sealed between the topsheet layer 20 and backsheet layer 30 along the perimeter of the absorbent core layer 41 along edge seal 35 formed by the application of heat and pressure to melt thermoplastic polymers located in the topsheet layer 20 and/or backsheet layer 30.

Additional layers that may be included upon the absorbent layer (core) and under, or above the topsheet layer(s) (if present) include one or more additional absorbent layers, surge layer(s), which are well known in the art to control a sudden onset of fluid, transfer delay layers and multifunctional multi-layered fluid control and absorbent materials, fluid guide layers, stabilizing layers, rigidifying layers and shaping layers. In manufacturing absorbent articles of the present invention which include the additional layers having portions aligned and desirably registered along the central longitudinal axis, it is desirable to provide a base sheet material for the additional layer(s) which can adequately serve two purposes, depending on the portion placement-within-product location, and the portion shape configuration. For the purposes of this application, a variety of base sheet materials may serve as the additional layer portions within a product. For example, such materials may be selected from nonwoven, woven, laminate and foam materials.

The selection of the additional layer base sheet material will depend on the primary function of the additional layer. Such acceptable nonwoven materials may include through-air bonded carded webs (TABCW) or thermally bonded carded webs (TBCW) for surge-type layers. In one embodiment, desirable surge layers are comprised of bicomponent fibers having a basis weight of between about 13 gsm and 60 gsm, as available from Dayuan Company of Beijing, China, and Sambo Company of Korea. Surge layers are further described in U.S. Pat. No. 5,364,382 to Latimer et al., and U.S. Pat. No. 5,843,063 to Anderson et al., each of which is hereby incorporated by reference in its entirety.

Multifunctional, multilayered airlaid materials/laminates are described for example in U.S. Pat. No. 4,640,810 to Laursen et al; U.S. Pat. No. 4,494,278 to Kroyer et al.; U.S. Pat. No. 5,527,171 to Soerensen et al., U.S. Pat. No. 4,375,448 to Appel et al., and U.S. Pat. No. 6,759,567 to Jackson et al., which are each hereby incorporated by reference in their entirety. An example of such airlaid materials would include for example, an airlaid laminate of bicomponent fiber and pulp having a basis weight of between about 30 and 300 gsm, desirably, having a basis weight of between about 50 and 200 gsm. Such materials are available from Buckeye Corp., TN, USA.

Additional absorbent or fluid guiding layers may be comprised of conventional foams, such as open and closed cell foams, or specialty foams. Such foams are for example described in U.S. Pat. No. 5,252,619 to Brownscombe et al.; U.S. Pat. No. 5,692,939 to DesMarais; U.S. Pat. No. 5,899,893 to Dyer et al.; U.S. Pat. No. 6,395,792 to Nagasuna et al.; U.S. Pat. No. 7,358,282 to Krueger et al. and U.S. 20060184150 to Noel, the entirety of which are each hereby incorporated by reference.

Other examples of additional layer materials which are contemplated for alignment in portions along the central longitudinal axis of an article include fluid guide layers to direct fluid via physical barrier features, recesses, apertures or openings to the absorbent core layer(s), pad shaping layers to alter the shaping of a pad during product use, rigidifying layers, or a combination of the foregoing layers.

It should be understood that while certain additional layers can be cut or otherwise separated into portions for placement along the longitudinal axis of an absorbent article as described herein, such as in an overnight pad or diaper, further additional layers can be included within an article, that are not cut or separated into portions, but are instead utilized as continuous planar additional layer sheets. For such additional layers, which may include further surge, absorbent core, fluid distribution, or other transfer delay layers, the dimensions of these further continuous sheet layers can be substantially similar to those referenced above with respect to the absorbent layer of the pad. However it will be appreciated that the dimensions of these further additional layers will often be slightly or significantly less than those of the overall pad 10 or article outer dimensions, in order to be contained therein.

The absorbent articles of the present invention may further include one or more components or elements as may be desired. By way of example, the absorbent article may optionally include slits, voids or embossing on the topsheet and/or absorbent core in order to improve fluid intake, fluid distribution, stiffness (bending resistance) and/or aesthetic appeal. As a specific example, embossing can extend into both the topsheet layer(s) and absorbent core layer(s) or layers contained therebetween. Examples of suitable embossing patterns and methods include, but are not limited to, those are described in U.S. Pat. No. 4,781,710 Megison et al.; U.S. Pat. No. 7,686,790 to Rasmussen et al., EP769284A1 to Mizutani et al.; and U.S. Pat. No. 7,145,054 to Zander et al. each of which are hereby incorporated by reference thereto in its entirety.

The personal care articles can, optionally, contain one or more additional elements or components as are known and used in the art including, but not limited to, the use of fold lines, individual wrappers, elasticated flaps that extend above the plane of the topsheet in use, additional independent wings such as about the ends, odor control agents, perfumes, and the use of ink printing on one or more surfaces of the topsheet, backsheet, wings or absorbent core. Still further additional features and various constructions are known in the art.

Desirably such additional layers that are to be separated into portions for alignment along a longitudinal axis, are passed through a series of roll cutters and the desired portions are sequentially cut from the base sheets. Desirably, the portions are cut; either one portion being cut from within the outer confines of the other portion, or alternatively, the two portions being cut such that they have mated edges, from within the larger sheet. In such a manner, the manufacturing material waste is reduced. The respective portions are then sequentially placed along the central longitudinal axis of either a layer that is to be later inserted within an article, along multiple layers, or directly within or on, the formed article itself. Prior to placement, such portions may be rotated or combined as noted herein. Desirably, such portions are cut and placed using known cutting and registration processes in order to assure consistent article formation. Cutting and registration concepts are described for example in U.S. Pat. No. 6,074,333 to Rajala et al., U.S. Pat. No. 6,059,710 to Rajala et al., and U.S. Pat. No. 6,165,306 to Rajala et al. each of which are hereby incorporated by reference thereto in its entirety.

For certain embodiments, progressively smaller cut-out portions can be stacked to form hump-like structures such as those described in GB 2370780 to Aschenbrenner, which is hereby incorporated by reference in its entirety. For other embodiments, the shape of the second portion may be cut from within the confines of a first portion, rotated and placed, to create a hump-like shape in the rear end of a product. For example, in one embodiment, an asymmetric-shaped cutout (second portion), such as a tear-drop shaped cutout, may be cut from a surrounding base sheet material that makes up the first portion, and such cutout can be rotated prior to being placed as a hump-like feature towards the rear end of a feminine hygiene article. In this situation, a tear-drop shaped opening can be placed in an additional layer, first portion, such that the wider end of a tear drop opening faces the front end of a pad. The tear drop shaped cutout of a second portion can then be rotated 180° and placed with the wider end of the cutout facing towards the rear end of such a pad.

Thus, while the invention has been described in detail with respect to specific embodiments and/or examples thereof, it will be apparent to those skilled in the art that various alterations, modifications and other changes may be made to the invention without departing from the spirit and scope of the same. It is therefore intended that the claims cover or encompass all such modifications, alterations and/or changes.

We claim:

1. An absorbent article having a longitudinal and transverse direction, said absorbent article including a topsheet layer, a backsheet layer and at least one absorbent layer sandwiched between said topsheet layer and said backsheet layer, wherein said absorbent layer includes at least first and second portions positioned along said longitudinal direction, said at least first and second portions being non-integral with any other layer within the article and spaced apart from one another along said longitudinal direction, wherein said portions are made from the same base sheet material, and further wherein said first portion defines a complete opening therein, and wherein said second portion is of a shape mated to fit entirely within said opening, wherein said second portion is separated from said first portion by a gap in said longitudinal direction, wherein said base sheet material is completely absent in said transverse direction at said gap.

2. The absorbent article of claim 1 wherein said first portion defines an oval opening.

3. The absorbent article of claim 1 wherein said article is selected from a feminine hygiene article, an adult incontinence article, a baby care article and a child care article.

4. The absorbent article of claim 3, wherein said article is a feminine hygiene overnight pad.

5. The absorbent article of claim 1, wherein said at least first and second discrete portions are located within the same horizontal plane.

6. The absorbent article of claim 1 wherein said second portion is of an oval shape.

7. The absorbent article of claim 1 wherein said first portion is located towards the front end of said article, and said second portion is located towards the rear end of said article and wherein said first portion is shaped to fit about a user's vaginal opening and said second portion is shaped to fit between a user's buttocks region.

8. The absorbent article of claim 7 wherein said first and second portions are of a color that can be seen through said topsheet of said article when viewed from the topsheet surface.

* * * * *